United States Patent
Sanborn et al.

(10) Patent No.: US 10,961,586 B2
(45) Date of Patent: Mar. 30, 2021

(54) MDM2-CONTAINING DOUBLE MINUTE CHROMOSOMES AND METHODS THEREFORE

(71) Applicant: Five3 Genomics, LLC, Santa Cruz, CA (US)

(72) Inventors: John Zachary Sanborn, Santa Cruz, CA (US); Charles Joseph Vaske, Santa Cruz, CA (US); Stephen Charles Benz, Santa Cruz, CA (US)

(73) Assignee: Five3 Genomics, LLC, Culver City, CA (US)

( * ) Notice: Subject to any disclaimer, the term of this patent is extended or adjusted under 35 U.S.C. 154(b) by 170 days.

(21) Appl. No.: 15/439,717

(22) Filed: Feb. 22, 2017

(65) Prior Publication Data

US 2017/0159133 A1 Jun. 8, 2017

Related U.S. Application Data

(62) Division of application No. 15/099,596, filed on Apr. 15, 2016, which is a division of application No. 14/363,789, filed as application No. PCT/US2012/068581 on Dec. 7, 2012.

(60) Provisional application No. 61/616,535, filed on Mar. 28, 2012, provisional application No. 61/568,513, filed on Dec. 8, 2011.

(51) Int. Cl.

| C12Q 1/68 | (2018.01) |
| C12Q 1/6886 | (2018.01) |
| G16B 20/00 | (2019.01) |
| G16B 30/00 | (2019.01) |
| G16B 40/00 | (2019.01) |
| G16H 50/20 | (2018.01) |
| C12Q 1/6869 | (2018.01) |

(52) U.S. Cl.
CPC ......... *C12Q 1/6886* (2013.01); *C12Q 1/6869* (2013.01); *G16B 20/00* (2019.02); *G16B 30/00* (2019.02); *G16B 40/00* (2019.02); *G16H 50/20* (2018.01); *C12Q 2600/106* (2013.01); *C12Q 2600/172* (2013.01)

(58) Field of Classification Search
USPC .................. 435/6.1, 6.11, 91.1; 436/94, 501; 536/23.1, 24.3, 24.33
See application file for complete search history.

(56) References Cited

U.S. PATENT DOCUMENTS

| 2002/0169564 A1 | 11/2002 | Delaney et al. |
| 2004/0002818 A1 | 1/2004 | Kulp et al. |
| 2004/0011674 A1 | 1/2004 | Theelen |
| 2004/0106141 A1 | 6/2004 | Mischel et al. |
| 2004/0111674 A1 | 6/2004 | Koleszar et al. |
| 2004/0132030 A1 | 7/2004 | Roy et al. |
| 2009/0183268 A1 | 7/2009 | Kingsmore |
| 2010/0136560 A1 | 6/2010 | Vogelstein et al. |
| 2010/0196898 A1 | 8/2010 | Sugarbaker et al. |
| 2010/0227768 A1 | 9/2010 | Wigler et al. |
| 2010/0286994 A1 | 11/2010 | Tebbs et al. |
| 2011/0098193 A1 | 4/2011 | Kingsmore et al. |
| 2012/0059670 A1 | 3/2012 | Zachary et al. |
| 2012/0066001 A1 | 3/2012 | Zachary et al. |
| 2014/0350130 A1 | 11/2014 | Sanborn et al. |
| 2017/0011167 A1 | 1/2017 | Sanborn et al. |

FOREIGN PATENT DOCUMENTS

| AU | 2015238811 A1 | 10/2015 |
| CA | 2 858 688 A1 | 6/2013 |
| CN | 1401778 A | 3/2003 |
| CN | 104094120 A | 10/2014 |
| CN | 107341364 A | 11/2017 |
| JP | 2001-125929 A | 5/2001 |
| JP | 2006-65501 A | 3/2006 |
| JP | 2013-531980 A | 8/2013 |
| JP | 2015-500034 A | 1/2015 |
| JP | 2016-195604 A | 11/2016 |
| JP | 6268230 B2 | 1/2018 |
| JP | 2018-75024 A | 5/2018 |
| JP | 2018-075024 A | 5/2018 |
| KR | 10-2015-0006413 A | 1/2015 |
| KR | 10-2016-0099726 A | 8/2016 |
| WO | 2009/054806 A1 | 4/2009 |
| WO | 2009/128714 A1 | 10/2009 |
| WO | 2011/149534 A2 | 12/2011 |

(Continued)

OTHER PUBLICATIONS

Anker et al., Detection of circulating tumour DNA in the blood (plasma/serum) of cancer patients. Cancer and Metastasis Reviews 18, 65-73, 1999. Hahn, Molecular biology of double-minute chromosomes .Bioessays, 15,477-484, 1993.*

Salt et al., Double Minute Chromosomes in Acute Myeloid Leukemia and Myelodysplastic Syndrome: Identification of New Amplification Regions by Fluorescence in situ hybridization and Spectral Karyotyping. Genes,Chromosomes & Cancer, 34, 42-47, 2002.*

Gebhart. Double minutes, cytogenetic equivalents of gene amplification, in human neoplasia—a review. Clin. Transl. Oncol., 7, 477-485, 2005.*

(Continued)

*Primary Examiner* — Frank W Lu

(74) *Attorney, Agent, or Firm* — Martin Fessenmaier; Umberg Zipser, LLP

(57) ABSTRACT

Contemplated systems and methods allow for computational genomic analysis using paired-end sequence analysis and split read refinement to thereby identify high-confidence breakpoints associated with high copy numbers and orientation of rearrangements, which is then the basis for full reconstruction of double minutes (DM). In especially preferred aspects, the DM will also include an oncogene or tumor suppressor gene, and/or may be found in blood or blood derived fluids.

9 Claims, 16 Drawing Sheets

(56) References Cited

FOREIGN PATENT DOCUMENTS

| | | |
|---|---|---|
| WO | 2011/107482 A9 | 1/2012 |
| WO | 2013/086424 A1 | 6/2013 |

OTHER PUBLICATIONS

"Double minute" from Wikipedia, the free encyclopedia. Printed on Mar. 3, 2019.*
Lenzi et al., NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16, 2014.*
Namdev et al., Challenges and approaches for Oral protein and peptide drug delivery. Research J. Pharm. and Tech., 9(3), 305-312, 2016.*
Rehman et al., Delivery of Therapeutic Proteins: Challenges and Strategies. Current Drug targets, 17, 1172-1188, 2016.*
Hillmer, A.M., et al., Comprehensive long-span paired-end mapping reveals characteristic patterns of structural variations in epithelial cancer genomes, Genome Research, 2011, pp. 665-675, vol. 21.
ISA/US, International Search Report and Written Opinion for International Application No. PCT/US2012/068581, dated Feb. 20, 2013, 12 pages.
Leary, R.J., et al., "Detection of Chromosomal Alterations in the Circulation of Cancer Patients With Whole-Genome Circulation," Sci Transl Med., Nov. 28, 2012: vol. 4, Issue 162, p. 162ra154 Sci. Transl. Med. DOI: 10.1126/scitranslmed.3004742.
Jahr et al., DNA Fragments in the Blood Plasma of Cancer Patients: Quantitations and Evidence for Their Origin from Apoptoticand Necrotic Cells. Cancer Research, 61, 1659-1665, 2001.
Greenman, G.D., et al., "Estimation of Rearrangement Phylogeny for Cancer Genomes," Genome Research, vol. 22, No. 2, Oct. 12, 2011.
Raphael, B.J., et al., "Reconstructing Tumor Amplisomes," Bioinformatics, vol. 20, No. Suppl. 1, Jul. 19, 2004.
Stephens, Philip J., "Massive Genomic Rearrangement Acquired in a Single Catastrophic Event During CancerDevelopment," Cell, vol. 144, No. 1, Nov. 24, 2010.
Bashir, Ali, et al., "Evaluation of Paired-End Sequencing Strategies for Detection of Genome Rearrangements InCancer," PLOS Computational Biology, vol. 4, No. 4, Apr. 25, 2008.
Chen, Ken, et al., "BreakDancer: An Algorithm for High-Resolution Mapping of Genomic Structural Variation,"Nature Methods, vol. 6, No. 9, Sep. 1, 2009.
Sanborn, J.Z., et al., "Double Minute Chromosomes in Glioblastoma Multiforme are Revealed by PreciseReconstruction of Oncogenic Amplicons," Cancer Research, vol. 73, No. 19, Aug. 12, 2013.
Jahr, S. et al., "DNA Fragments in the Blood Plasma of Cancer Patients: Quantitations and Evidence for Their Origin From Apoptotic and Necrotic Cells", Cancer Research, vol. 61, pp. 1659-1665, Feb. 15, 2001.
Storlazzi, C.T., et al., "MYC-Containing Double Minutes in Hematologic Malignancies: Evidence in Favor of the Episome Model and Exclusion of MYC as the Target Gene," Human Molecular Genetics, vol. 15, No. 6, pp. 933-942, Feb. 1, 2006.
Jakupciak et al, Performance of mitochondrial DNA mutations detecting early stage cancer. BMC Cancer, 8, 285, 2008.
Strolazzi et al., "Gene amplification as double minutes or homogeneously staining regions in solid tumors: Originand structure", Genome Research, vol. 20, pp. 1198-1206 (2010).
Barker, Double minutes in human tumor cells. Cancer Genet Cytogenet., 5, 81-94, 1982.
Hahn, Molecular biology of double-minute chromosomes. Bioessays, 15, 477-484, 1993.
Final Office Action received for U.S. Appl. No. 15/439,717, dated Aug. 20, 2019, 13 pages.
Non-Final Office Action received for U.S. Appl. No. 14/363,789, dated Oct. 21, 2016, 21 pages.
Final Office Action received for U.S. Appl. No. 14/363,789, dated Apr. 21, 2017, 16 pages.
Non-Final Office Action received for U.S. Appl. No. 14/363,789, dated Nov. 16, 2017, 13 pages.
Final Office Action received for U.S. Appl. No. 14/363,789, dated Jul. 19, 2018, 19 pages.
Non-Final Office Action received for U.S. Appl. No. 14/363,789, dated Jan. 9, 2019, 20 pages.
Final Office Action received for U.S. Appl. No. 14/363,789, dated Sep. 17, 2019, 17 pages.
"Omics" from Wikipedia, the free encyclopedia. Printed on Jan. 20, 2018.
Kawasaki et al., "BCL2L2 is a Probable Target for a Novel 14q 11.2 Amplification Detected in a Non-Small Cell Lung Cancer Cell Line", Cancer Sci, vol. 98, No. 7, Jul. 2007.
Araki et al., "Glioblastoma Multiforme with a Peculiar Chomosomal Aberration—Double Minute Chromosomes" Kurashiki Central Hospital, Department of Neurosurgery, Apr. 15, 1986.
Alekseyev et al., "Breakpoint Graphs and Ancestral Genome Reconstructions" Genome Research, www.genome.org, Jan. 2009.
Srivastava et al., DNA Double-Strand Break Repair Inhibitors as Cancer Therapeutics. Chemistry & Biology 22, 17-29, 2015.
Non-Final Office Action received for U.S. Appl. No. 15/099,596, dated Jan. 26, 2018, 12 pages.
Final Office Action received for U.S. Appl. No. 15/099,596, dated Jul. 10, 2018, 20 pages.
Non-Final Office Action received for U.S. Appl. No. 15/099,596, dated Jan. 31, 2019, 15 pages.
Final Office Action received for U.S. Appl. No. 15/099,596, dated May 23, 2019 , 17 pages.
Notice of Reasons for Refusal received for J.P. Application No. 2017-247929, dated Jan. 22, 2019, 4 pages.
Notice of Reasons for Refusal received for J.P. Application No. 2017-247929, dated Sep. 17, 2019, 4 pages.
Hillmer et al. "Comprehensive Long-Span Paired-End-Tag Mapping Reveals Characteristic Patterns of Structural Variations in Epithelial Cancer Genomes," Genome Research, Apr. 19, 2011 (Apr. 19, 2011 ), vol. 21, pp. 665-675 and Supplemental Information.
Campbell et al. "Identification of somatically acquired rearrangements in cancer using genome-wide massively parallel paired-end sequencing," Nature Genetics, Apr. 2008 (Apr. 27, 2008),vol. 40, No. 6, pp. 722-729 and Supplemental Information.
Non-Final Office Action received for U.S. Appl. No. 14/363,789 dated May 15, 2020, 42 pages.
Suzuki et al., Amplification and Overexpression of mdm2 Gene in Ependymomas. Modern Pathology, 13, 548-553, 2000.
Kato et al., Analysis of MDM2 Amplification: Next-Generation Sequencing of Patients With Diverse Malignancies, JCO Precision Oncology, DOI: 10.1200/P0.17.00235, published online Jul. 13, 2018.
Hunter et al., Reliability of Differential PCR for the Detection of EGFR and MDM2 Gene Amplification in DNA Extracted from FFPE Glioma Tissue. Journal of Neuropathology & Experimental Neurology, 54, 57-64, 1995.
Kato et al., Revisiting Epidermal Growth Factor Receptor (EGFR) Amplification as a Target for Anti-EGFR Therapy: Analysis of Cell-Free Circulating Tumor DNA in Patients With Advanced Malignancies. JCO Precis Oncology, doi: 10.1200/P0.18.00180, published online on Jan. 22, 2019.
Supplementary Table 3: A list of oncogenes and tumor suppressors used in the comparison of gene functional groups. Printed on May 11, 2020.
Definitions for "Oncogenes and tumor suppressor genes" from American Cancer Society. Printed on May 11, 2020.
Notice of Allowance received for U.S. Appl. No. 15/099,596 dated May 8, 2020, 16 pages.
Examination Report received for Australian Patent Application No. 2012347522 dated Mar. 23, 2015, 3 pages.
Notice of Acceptance received for Australian Patent Application No. 2012347522 dated Jul. 15, 2015, 3 pages.
Examination Report received for Australian Patent Application No. 2015238811 dated Nov. 24, 2016, 3 pages.

(56) References Cited

OTHER PUBLICATIONS

Notice of Acceptance received for Australian Patent Application No. 2015238811 dated May 23, 2017, 3 pages.
Office Action received for Canadian Patent Application Serial No. 2858688 dated Oct. 30, 2015, 3 pages.
Office Action received for Canadian Patent Application Serial No. 2858688 dated Jun. 17, 2016, 3 pages.
Office Action received for Canadian Patent Application Serial No. 2858688 dated May 10, 2017, 4 pages.
Office Action received for Canadian Patent Application Serial No. 2858688 dated Apr. 6, 2018, 6 pages.
Office Action received for Canadian Patent Application Serial No. 2858688 dated Feb. 12, 2019, 6 pages.
First Office Action received for Chinese Patent Application Serial No. 201280068336 dated Mar. 26, 2015, 18 pages (Including English Translation).
Second Office Action received for Chinese Patent Application Serial No. 201280068336 dated Dec. 18, 2015, 14 pages (Including English Translation).
Third Office Action received for Chinese Patent Application Serial No. 201280068336 dated Jun. 28, 2016, 8 pages (Including English Translation).
First Office Action received for Chinese Patent Application Serial No. 201710189263.5 dated Mar. 16, 2020, 7 pages (Including English Translation).
Extended European Search Report received for European Patent Application Serial No. 12854939.1 dated May 13, 2015, 12 pages.
Communication Pursuant to Article 94(3) EPC received for European Patent Application Serial No. 12854939.1 dated Aug. 11, 2017, 5 pages.
Summons to attend oral proceedings pursuant to Rule 115(1) EPC received for European Patent Application Serial No. 12854939.1 dated Apr. 3, 2020, 11 pages.
Notice of Reasons for Refusal received for Japanese Patent Application Serial No. 2014546145 dated Jul. 28, 2015, 16 pages (Including English Translation).
Decision of Reasons for Refusal received for Japanese Patent Application Serial No. 2014546145 dated Mar. 1, 2016, 11 pages (Including English Translation).
Notice of Reasons for Refusal received for Japanese Patent Application Serial No. 2014546145 dated Oct. 18, 2016, 10 pages (Including English Translation).
Decision to Grant a Patent received for Japanese Patent Application Serial No. 2014546145 dated Dec. 6, 2016, 5 pages (Including English Translation).
Notice of Reasons for Refusal received for Japanese Patent Application Serial No. 2016126581 dated Jun. 6, 2017, 3 pages (Including English Translation).
Decision to Grant a Patent received for Japanese Patent Application Serial No. 2016126581 dated Nov. 28, 2017, 5 pages (Including English Translation).
Notice of Reasons for Refusal received for Japanese Patent Application Serial No. 2017247929 dated Sep. 17, 2019, 8 pages (Including English Translation).
Decision to Grant a Patent received for Japanese Patent Application Serial No. 2017247929 dated Feb. 10, 2020, 5 pages (Including English Translation).
Vogt, "Molecular structure of double-minite chromosomes bearing amplified copies of the spidermal growth factor receptor gene in gliomas", PANS, vol. 101, No. 31, pp. 11368-11373.
Notification of Reason of Refusal received for Korean Patent Application No. 10-2014-7016584 dated Sep. 8, 2015, 9 pages (Including English Translation).
Notice of Final Rejection received for Korean Patent Application No. 10-2014-7016584 dated May 10, 2016, 7 pages (Including English Translation).
Notification of Reason of Refusal received for Korean Patent Application No. 10-2014-7016584 dated Sep. 8, 2016, 15 pages (Including English Translation).
Notification of Reason of Refusal received for Korean Patent Application No. 10-2016-7021597 dated Oct. 18, 2017, 15 pages (Including English Translation).
Notice of Final Rejection received for Korean Patent Application No. 10-2016-7021597 dated Apr. 23, 2018, 7 pages (Including English Translation).
Istrail et al., "Computational Molecular Biology", An Algorithmic Approach, 2000, 332 pages.
Leary et al., "Detection of Chromosomal Alterations in the Circulation of Cancer Patients with Whole-Genome Sequencing", Science Translational Medicine, 2012, vol. 4, No. 162, pp. 1-12.
"Gene Transfer Research: The Evolution of the Clinical Science", National Library of Medicine, 2015, 16 pages.
Sindi et al., "A geometric approach for classification and comparison of structural variants", Bioinformatics, vol. 25, No. 12, Jun. 15, 2009, pp. i222-i230 (Cited from Specification).
Chen et al., "BreakDancer: an algorithm for high-resolution mapping of genomic structural variation", Nat. Methods, Sep. 2009, vol. 6, No. 9, pp. 677-681 (Cited from Specification).
Bass et al., "Genomic sequencing of colorectal adenocarcinomas identifies a recurrent VTI1A-TCF7L2 fusion", Nature Genetics, 2011, vol. 43, No. 10, 15 pages (Cited from Specification).
Leary et al.,"Development of personalized tumor biomarkers using massively parallel sequencing", Sci Transl Med., Feb. 24, 2010, vol. 2, No. 20, 15 pages (Cited from Specification).
Paterlini-Brechot et al., "Circulating tumor cells (CTC) detection: clinical impact and future directions", Cancer Letters, 2007, vol. 253, pp. 180-204 (Cited from Specification).
Fan et al., "Frequency of double minute chromosomes and combined cytogenetic abnormalities and their characteristics", J Appl Genetics, 2011, vol. 52, pp. 53-59 (Cited from Specification).
The Cancer Genome Atlas (TCGA) Research Network, "Comprehensive genomic characterization defines human glioblastoma genes and core pathways", Nature, 2008, vol. 455, No. 7216, 23 pages (Cited from Specification).
Fakharzadeh et al., "Structure and organization of amplified DNA on double minutes containing the mdm2 oncogene", Genomics, 1993, vol. 15, No. 283-290 (Cited from Specification).
Skog et al., "Glioblastoma microvesicles transport RNA and proteins that promote tumour growth and provide diagnostic biomarkers", Nat Cell Biol., 2008, vol. 10, No. 12, pp. 1470-1476 (Cited from Specification).
Balaj et al., "Tumour microvesicles contain retrotransposon elements and amplified oncogene sequences", Nature communications, 2010, vol. 2, No. 180, pp. 1-9 (Cited from Specification).
Kobaldt et al., "SAM, BAM, Thank you Ma'am", massgenomics.org/2009/7/sam-bam-thank-you-maam, 4 pages.
Notice of Allowance received for U.S. Appl. No. 15/099,596 dated Dec. 10, 2019, 7 pages.
Intention to grant received for European Patent Application Serial No. 12854939 dated Sep. 23, 2020, 8 pages.

* cited by examiner

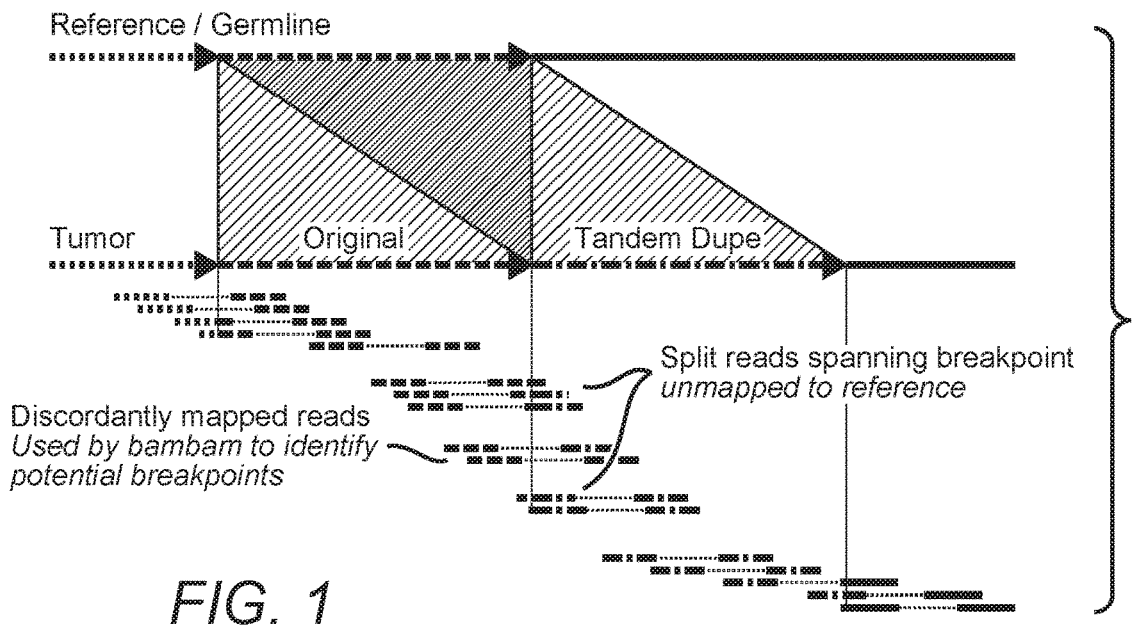
FIG. 1
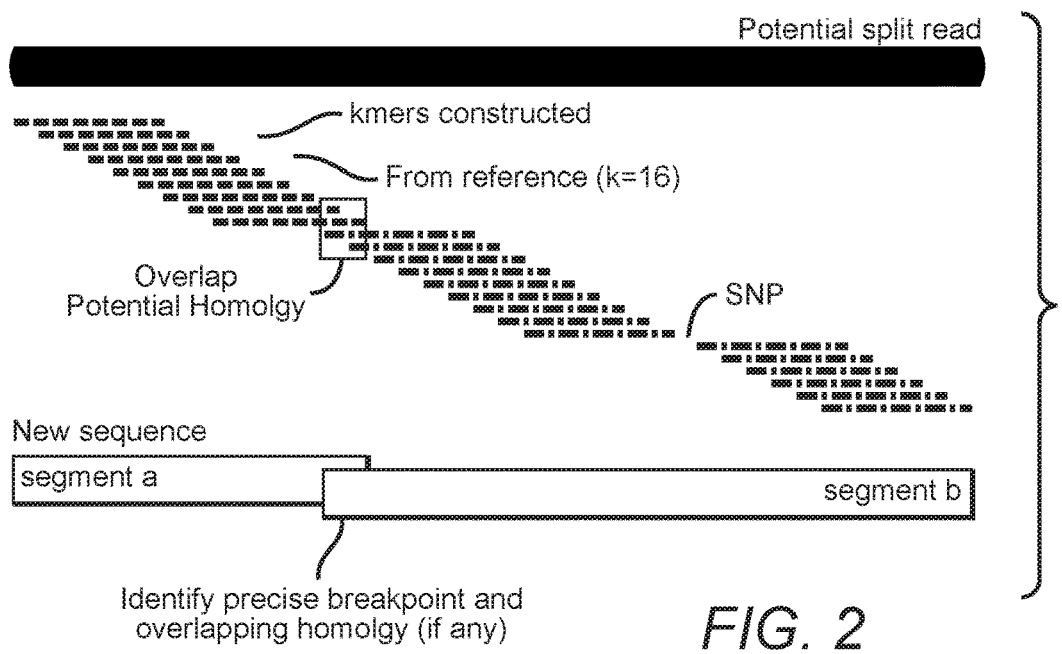
FIG. 2
FIG. 3
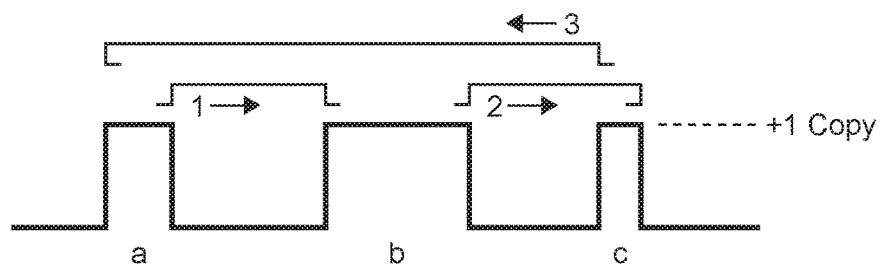

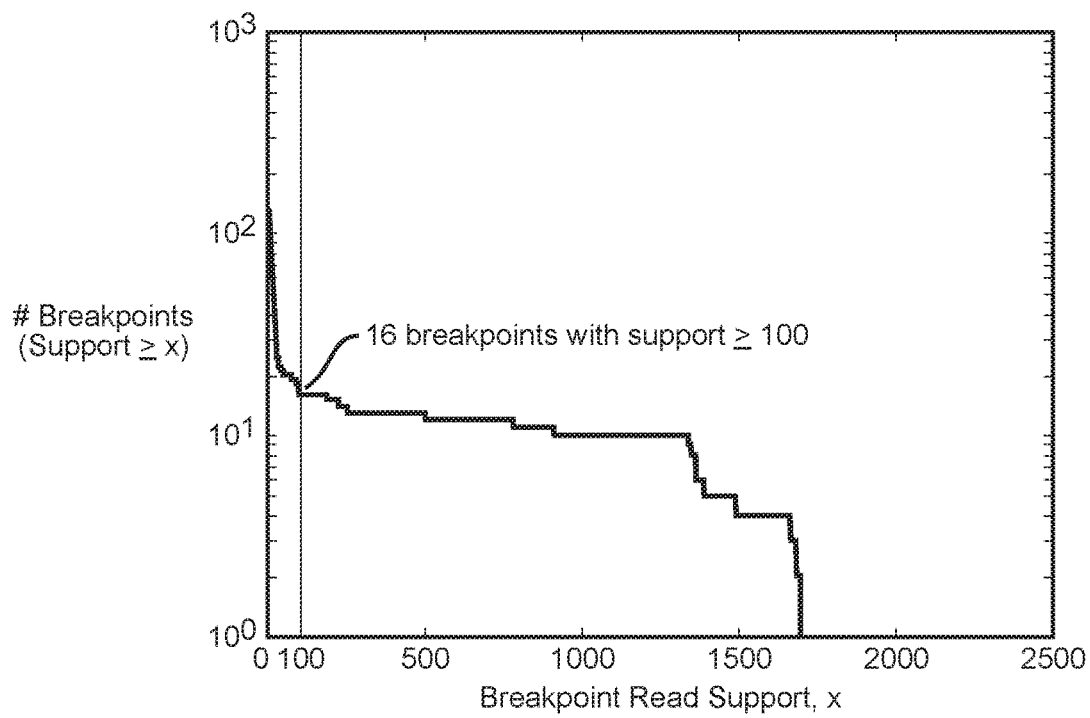
FIG. 4
FIG. 9
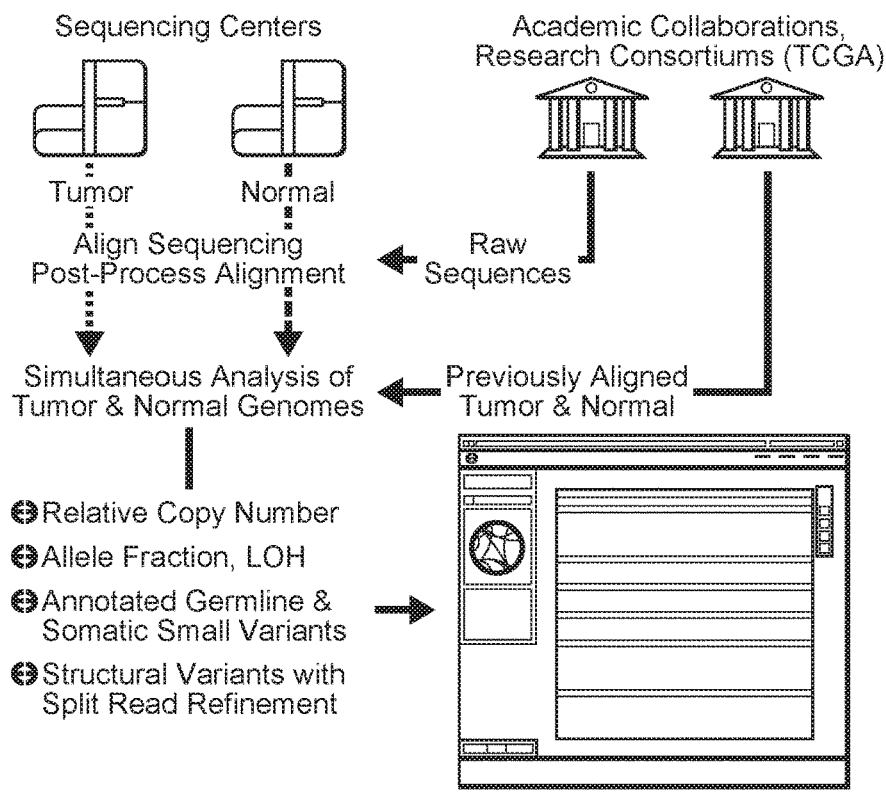

FIG. 11B-1

MDM2-CONTAINING DOUBLE MINUTE CHROMOSOMES AND METHODS THEREFORE

This application is a divisional of U.S. application Ser. No. 15/099,596, filed Apr. 15, 2016, which is a divisional of U.S. application Ser. No. 14/363,789, filed Jun. 6, 2014, which is a U.S. national phase application of PCT Application Number PCT/US12/68581, filed Dec. 7, 2012, which claimed the benefit of priority to U.S. provisional patent application Ser. No. 61/616,535 filed Mar. 28, 2012 and 61/568,513 filed Dec. 8, 2011. These applications and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is molecular diagnostics, especially as it relates to analysis and identification of genomic rearrangements.

BACKGROUND

The introduction of whole-genome sequencing has provided researchers with an unprecedented ability to measure the complex state of genomic rearrangements characteristic of most cancers. Numerous methods for inferring structural variation from paired-end sequencing data have been developed (Bioinformatics(2009); 25: i222-i230; Nature Methods 2009 August; 6:677-681; Nature Genetics 2011 March; 43:964-968), but the structural variants called by such methods are often considered only in isolation, used primarily to identify potential fusion genes. The difficulty in discovering all true structural variants and filtering out false positives makes it hard to use the output of currently known methods to reassemble large regions of the tumor genome. Such difficulties are particularly unfortunate as proper tumor genome assemblies help reveal the complex structure of the tumor genome and could be used to infer a mechanism by which somatic alterations such as amplifications of oncogenes and deletions of tumor suppressors occur.

Rapidly decreasing cost and increased data resolution of whole-genome sequencing also promises the emergence of new classes of cancer diagnostics from blood. For example, Leary et al. (SciTransl Med 2010 Febuary; 2(20):20ra14) developed a personalized analysis of rearranged ends (PARE), which uses somatic rearrangements to build a blood-based diagnostic assay for recurrence. While this novel method provides a powerful framework for monitoring, analysis of biopsied tumor tissue is typically needed to find specific markers to be measured in blood. Other monitoring techniques, such as measuring circulating tumor cells, require significant enrichment efforts that are only feasible when tumors with metastatic potential are present (Cancer Lett. 2007 August; 253(2):180-204). Both of these techniques present technical challenges that make them unsuitable for initial tumor diagnosis.

It is well documented that double-stranded DNA can become highly amplified and circularized in the cytoplasm of cells, forming what is known as double minutes (Cancer Genet. Cytogenet. 1982 Febuary; 5(1):81-94). Double minutes (DMs) have been shown to confer resistance to certain drugs, as well as pass along this resistance non-uniformly to daughter cells. They have been observed up to a few megabases in size, and contain chromatin similar to actual chromosomes, but lack the centromere or telomeres found in normal chromosomes. Since DMs lack centromeres, they are randomly distributed to daughter cells during cell division, and they are generally lost in future generations unless there is some selective pressure to maintain them. However, the random distribution of DMs also provides a simple mechanism to quickly amplify an oncogenic DM in successive generations, where cells may accumulate hundreds of copies of the double minute. Though the frequency of double minutes in glioblastoma multiforme (GBM) is largely unknown, a recent study by Fan et al. (J. Appl. Genet. 2011 Febuary; 52(1):53-59) has identified neuroblastomas as having the second highest rate of DMs, offering the possibility that perhaps some of the frequently amplified oncogenes in GBM tumors can be explained by the formation and accumulation of oncogenic double minutes.

Despite the fact that DMs were originally identified over thirty years ago, there is no evidence in the literature that a comprehensive sequence analysis of DMs has been done. Thus, there is still a need for improved diagnostic methods, and especially improved methods for genetic analysis of neoplastic tissue that may be associated with presence of DMs.

SUMMARY OF THE INVENTION

The inventive subject matter is drawn to methods and computational systems in which whole genome paired-end sequence analysis enables rapid and comprehensive identification of genetic rearrangements via identification of high-confidence breakpoints and associated high copy numbers to fully reconstruct intact DMs that typically contain highly amplified oncogenes associated with the neoplasm.

In one especially preferred aspect of the inventive subject matter, a method of analyzing genomic data that includes a step of determining a relative copy number between a tumor genomic sequence and a matched normal genomic sequence, and a further step of identifying putative breakpoints in the tumor genomic sequence and the matched normal genomic sequence. In another step, the putative breakpoints are refined, preferably using fragmenting the tumor genomic sequence and comparing the fragments with a reference database, to identify a breakpoint location and an orientation of the tumor genomic sequence, and in another step, a read support threshold (e.g., user-determined) is used to confirm the breakpoint as a significant breakpoint. In a still further step, the relative copy number, the significant breakpoint, and the orientation are used to determine a genomic arrangement having a circular solution (which may be indicative of a double minute chromosome).

In especially preferred aspects, the step of determining the relative copy number is performed using dynamic windowing and/or wherein the step of identifying putative breakpoints is performed using discordant paired reads. While not limiting to the inventive subject matter, it is generally preferred that the genomic arrangement is determined by generating a breakpoint graph and solving the breakpoint graph to arrive at the circular solution.

In further contemplated aspects, the tumor genomic sequence is from a solid tumor, while the tumor genomic sequence is isolated from genetic material present in a biological fluid (e.g., blood, serum, plasma, aspirate, etc.). For example, the solid tumor may be glioblastoma multiforme or a non-small cell lung cancer.

Viewed from a different perspective, contemplated methods of analyzing genomic data may include a step of associating a copy number of a tumor genomic sequence with a breakpoint in the tumor genomic sequence upon reaching a read support threshold (preferably user-defined) for the breakpoint, and a step of determining orientation of the tumor genomic sequence. Such methods will further include a step of determining genomic arrangement using the copy number, position of the breakpoint, and orientation of the tumor genomic sequence. Typically, but not necessarily, the step of determining genomic arrangement is performed by generating a breakpoint graph using the copy number of the tumor genomic sequence, the position of the breakpoint within a genome, and the orientation of the tumor genomic sequence, wherein in the breakpoint graph the copy number is expressed as an edge and wherein the breakpoint position is expressed as a vertex.

In another aspect of the inventive subject matter, a method of analyzing genomic data of a solid tumor will include a step of identifying the solid tumor as a tumor of which at least a portion of a tumor genome is present in a biological fluid, and another step of obtaining from a patient the biological fluid and isolating the at least portion of the tumor genome, which is then used to analyze the genomic data as described above and in the detailed description. Most typically, the portion of the tumor genome is present as a double minute chromosome that may include an oncogene or a tumor suppressor gene. Thus, contemplated methods may also include a step of identifying an oncogene or a tumor suppressor gene within the isolated at least portion of the tumor genome. In this event, the method will also comprise a step of treating or advising to treat the patient using a pharmaceutical regimen that targets the oncogene or tumor suppressor gene.

In yet another aspect of the inventive subject matter, a method of analyzing genomic data of a solid tumor (e.g., is glioblastoma multiforme or non-small cell lung cancer) will include a step of obtaining from a patient a biological fluid (e.g., blood, serum, plasma, etc.) and isolating at least a portion of a tumor genome from the biological fluid, and a further step of determining if a region surrounding an oncogene (e.g., wild type or mutant form of EGFR, c-Myc, or MDM2) exhibit a clustered pattern of breakpoints indicative of an amplified double minute. Determination is preferably performed as described above and as in the detailed description.

Therefore, the inventors also contemplate a method of de-novo diagnosing a neoplastic disease (e.g., gastric cancer, colon cancer, prostate cancer, lung cancer, leukemia, or breast cancer) that includes a step of obtaining a biological sample from a patient and isolating a nucleic acid from the sample, and a further step of analyzing the nucleic acid for a copy number of a genomic sample and a breakpoint in the genomic sample. In a still further step, the copy number of the genomic sequence is associated with the breakpoint in the genomic sequence upon reaching a read support threshold for the breakpoint, and orientation of the genomic sequence is determined. In yet another step, genomic arrangement is determined using the copy number, position of the breakpoint, and the orientation of the genomic sequence, and the so identified genomic arrangement is used to determine likelihood for the neoplastic disease. In at least some aspects of the inventive subject matter, the genomic arrangement is identified as a double minute, and/or as including an oncogene or tumor suppressor gene.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 is an exemplary graph depicting initial identification of a putative structural variant according to the inventive subject matter.

FIG. 2 is an exemplary graph depicting refined analysis of a breakpoint in the putative structural variant of FIG. 1.

FIG. 3 is an exemplary breakpoint graph according to the inventive subject matter.

FIG. 4 is an exemplary histogram of read support for somatic breakpoints.

FIG. 9 is schematic exemplarily depicting configurations and systems for genomic analysis according to the inventive subject matter.

FIGS. 10A-1, 10A-2, and 10B-1, 10B-2 are exemplary illustrations for rearrangement patterns and corresponding circular solutions in a first tumor sample.

FIGS. 11A-1, 11A-2, and 11B-1, 11B-2 are exemplary illustrations for rearrangement patterns and corresponding circular solutions in a second tumor sample.

FIGS. 12A-1, 12A-2, and 12B are exemplary illustrations for rearrangement patterns and corresponding circular solutions in a further tumor samples.

DETAILED DESCRIPTION

Figure 5:
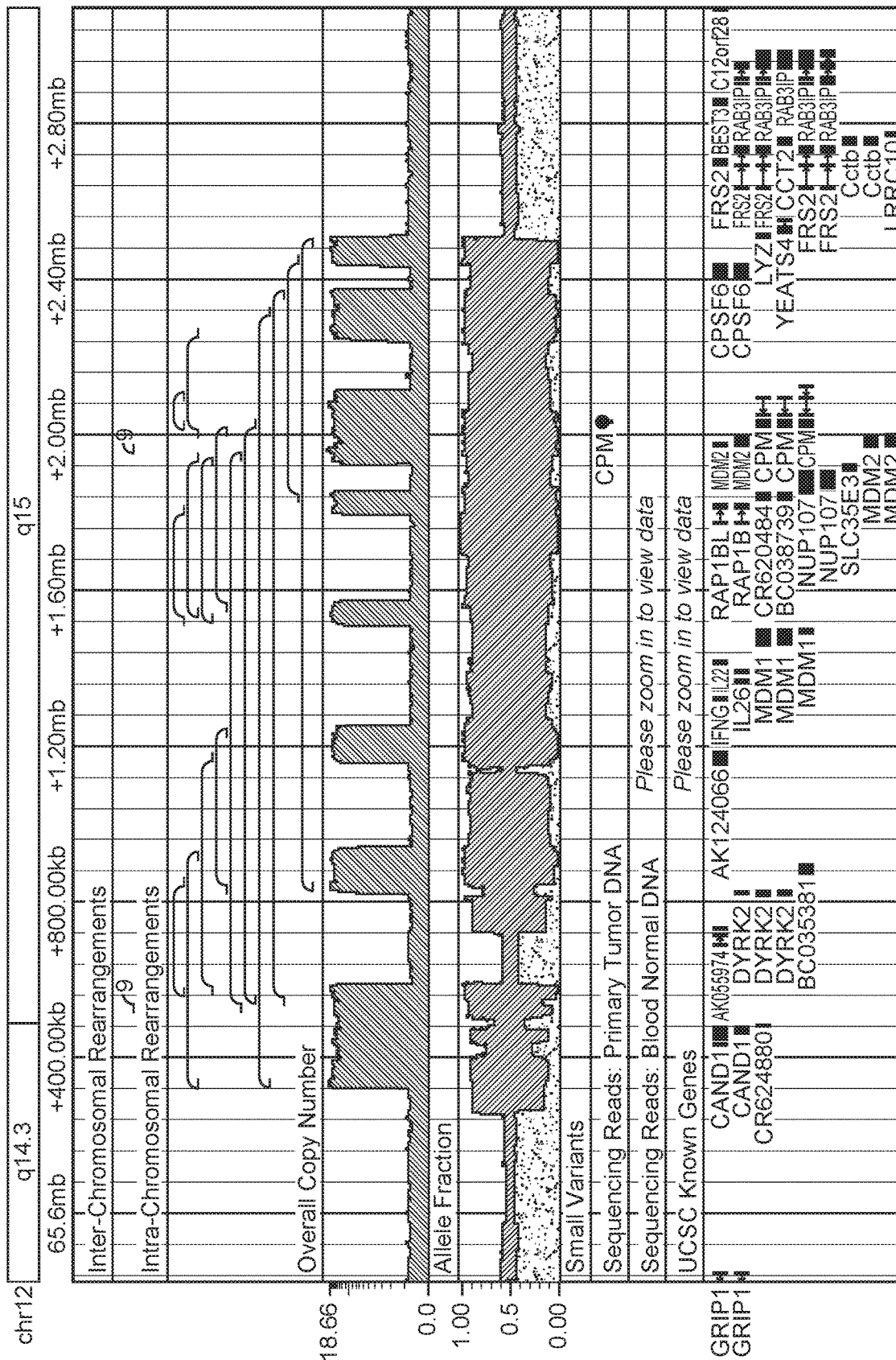
FIG. 5 is an exemplary genome browser display depicting high copy numbers and highly supported breakpoints.

The inventors have discovered that genomic analysis can be performed to identify one or more DMs from whole genomic sequence data by identifying high-confidence breakpoints and associated high copy numbers, and by analysis of the data to arrive at a circular solution in a rearrangement plot.

To that end, the inventors developed and used algorithms capable of identifying high-confidence breakpoints, fragment orientation, and analysis of whole-genome sequencing data, which ultimately allows full reconstruction of intact DMs that in many cases contain highly amplified oncogenes. For example, the inventors used two glioblastoma multiforme (GBM) sample sequences by The Cancer Genome Atlas (Nature 2008 October; 455(7216):1061-1068) for full reconstruction of intact DMs. In addition, the inventors also discovered evidence for DMs in blood samples of the same patients, indicating that GBM tumor cells are shedding oncogenic DMs into the bloodstream. Particularly preferred algorithms include BAMBAM, which is described in US 2012/0066001 and US 2012/0059670, both of which are incorporated by reference herein. Methods and computational systems presented herein enable rapid and comprehensive identification of genetic rearrangements via whole genome paired-end sequencing. More particularly, the inventors employed the below described systems and methods to analyze whole-genome sequencing data to so arrive at a result that represents describes fully reconstructed DMs.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

In one exemplary aspect of the inventive subject matter, copy numbers are determined and structural variations inferred as follows.

Computing relative copy number between tumor and matched normal: Tumor vs. normal relative copy number is calculated using a dynamic windowing approach that expands and contracts the window's genomic width according to the read coverage in either the tumor or normal sequencing datasets. The process is initialized with a window of zero width. Each read that exceeds certain quality thresholds (e.g., read mapping quality) from both the tumor and matched normal sequence data will be tallied into tumor counts, $N_{tumor}$, and normal counts, $N_{normal}$, respectively. The start and stop positions of the first read defines the initial window's width, and as more reads are collected, the window's width expands to contain the minimum start and maximum stop positions of all reads processed.

A relative copy number calculation is made when the following condition is met: the read counts from either tumor or matched normal datasets exceed both a user-defined upper and a lower threshold that is fixed at 100 reads. When this occurs, the window's size and location, the raw read counts $N_{tumor}$, $N_{normal}$, and the relative copy number calculation $N_{tumor}/N_{normal}$, are recorded. All values are then reset for the next collection and computation. By tailoring the size of the $N_{normal}$ window according to the local read coverage, this method produces large windows in regions of low coverage to improve signal-to-noise ratio, while regions that are highly amplified will produce smaller windows, increasing the resolution of amplicon boundaries.

Figures 1, 10A:
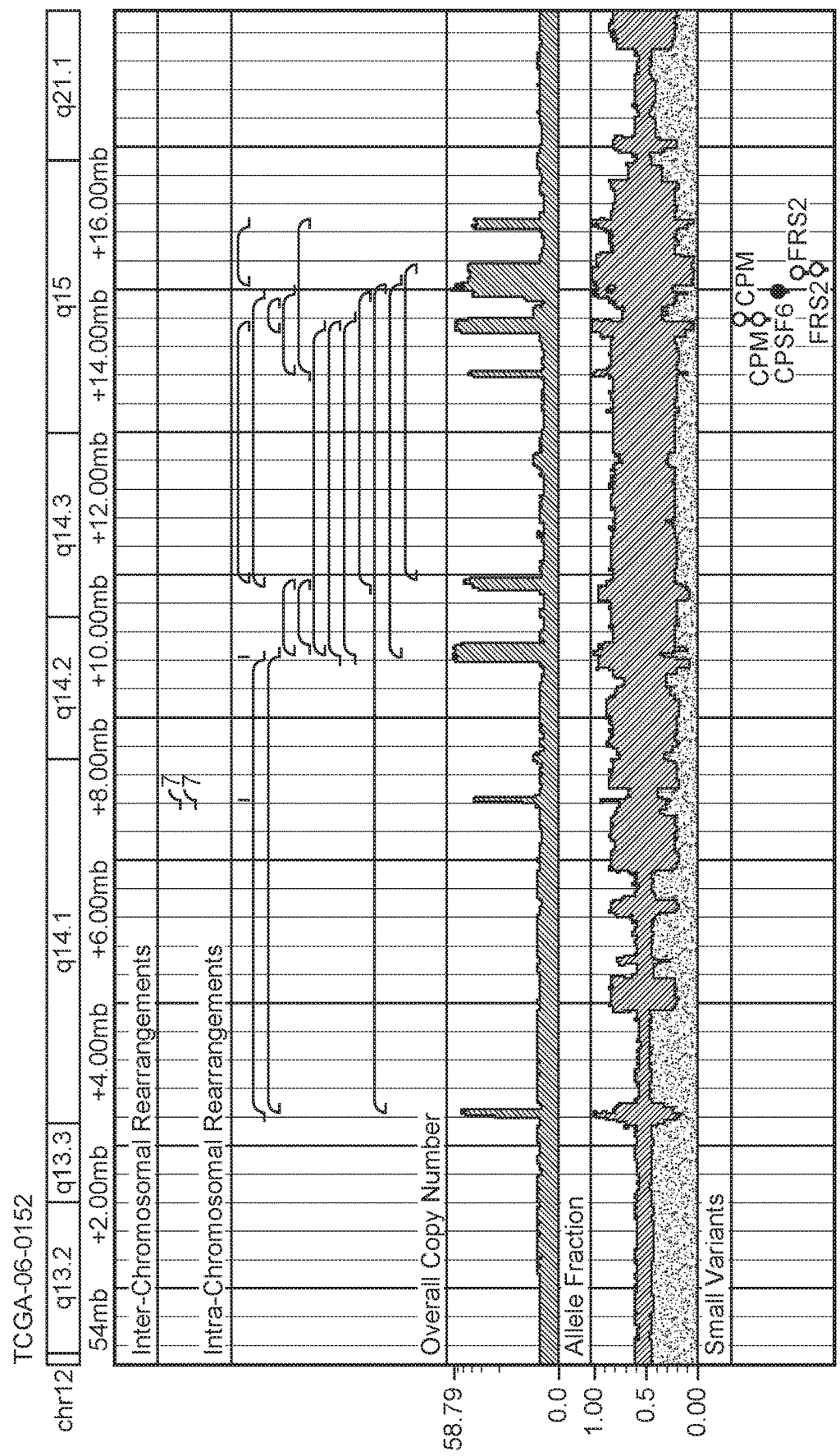

Inferring regions of structural variation using paired-end clustering: To identify putative intra- and inter-chromosomal rearrangements, bambam searches for discordant paired reads stored in a pair of coordinate-sorted BAM files, one from the tumor sample and the other from the matched normal sample, where each read in the discordant pair map to disparate regions of the reference sequence. Intra-chromosomal discordant pairs are those that have an abnormally large insert size (i.e., the genomic distance on the reference separating the paired reads exceeds a user-defined threshold) or those that map in an incorrect orientation (i.e., inversion). Inter-chromosomal discordant pairs are defined by paired reads that map to different chromosomes. An overview of this process is shown in FIG. 1, which schematically depicts an overview of structural variation calling. The initial identification of a putative structural variant is identified by bambam using discordantly mapped read pairs, where both reads fully map to the reference genome, but do so in an abnormal, non-reference manner. The putative breakpoints found by bambam are then refined by a program called bridget using any available split reads in the neighborhood of the breakpoint.

All discordant paired-end reads from both tumor and normal datasets are clustered according to their genomic locations to define an approximate genomic region where the breakpoint is believed to be. The aggregation process comprises grouping together the reads that overlap other reads on both sides of the putative breakpoint and have the identical orientation, while keeping track of the number of reads that came from tumor and normal datasets. When the number of overlapping discordant pairs in a cluster exceeds a user-defined threshold, the breakpoint that describes the rearrangement is defined and recorded in the output.

Breakpoints are classified as "somatic" if they are significantly supported by reads from the tumor dataset. A minimal amount of read support for "somatic" breakpoints from the matched normal dataset is allowed to accommodate cases where some level of tumor DNA is present in the matched normal sample. This may occur when highly amplified regions present in a solid tumor's DNA are shed off into the bloodstream at low, but detectable levels. Alternatively, in the case of hematological cancers, it is expected that there will be a high level of tumor introgression in the matched normal sample (typically skin). The amount of support for somatic breakpoints allowed in the matched normal dataset can be adjusted according to the amount of tumor "contamination" expected in the matched normal sample. "Germline" breakpoints are those that have significant support in both tumor and matched normal datasets or only have support in the matched normal dataset. These are not considered in this analysis, as these rearrangements are not pertinent to the problem at hand. Also, many of these breakpoints are believed to be spurious, due to artifacts induced by the sequencing instrument, sample preparation (such as whole-genome amplification), or a systematic bias in the short-read mapping algorithm employed.

Refinement of structural variation using split-reads: The breakpoints found initially by bambam are approximate, in that they use fully-mapped reads that, by their nature, do not substantially overlap the actual junction of the breakpoint, since it represents sequence not present in the reference (or the matched normal dataset, in the case of a somatic rearrangement). To refine the location of the breakpoint, a program called bridget was developed.

Bridget is given the approximate breakpoint found by bambam and searches for all unaligned reads that are anchored near the putative breakpoint by a fully-mapped mate. Each of these unmapped reads have the potential to be a "split read" that overlaps the rearrangement's breakpoint junction. Localized genomic sequences surrounding both sides of the breakpoint are broken up into a set of unique tiles (currently tile size=16 bp), and a tile database of the tile sequences and their location in the reference genome is built. A similar tile database is constructed for each unaligned read, by breaking up the read into tiles of the same size and noting their location within the read. Comparing the reference tile database and the unaligned tile database, the genomic location of each unaligned tile in the reference is determined. "Dual-spanning sets" of these locations are computed by determining the maximal set of tiles that are contiguous in both the reference and unaligned reads, one for each side of the breakpoint.

The minimum and maximum genomic locations of the dual-spanning sets in reference coordinates precisely determine the breakpoint location, as well as the orientation (or strandedness) of both sides of the junction. With the information describing the left and a right boundaries of the breakpoint, the rearranged sequence is fully defined, i.e. the left side is defined by (e.g., chromosome=chr1, location=1000 bp, strand=forward) and the right side is defined by (e.g., chromosome=chr5, location=500,000 bp, strand=reverse). The sequence homology of the breakpoint (i.e., a short sequence, such as "CA," observed to be identical on both boundaries of the breakpoint, but is observed only once in the aligned read at the junction of the two sequences) is also determined from these dual-spanning sets.

Figures 2, 10A:
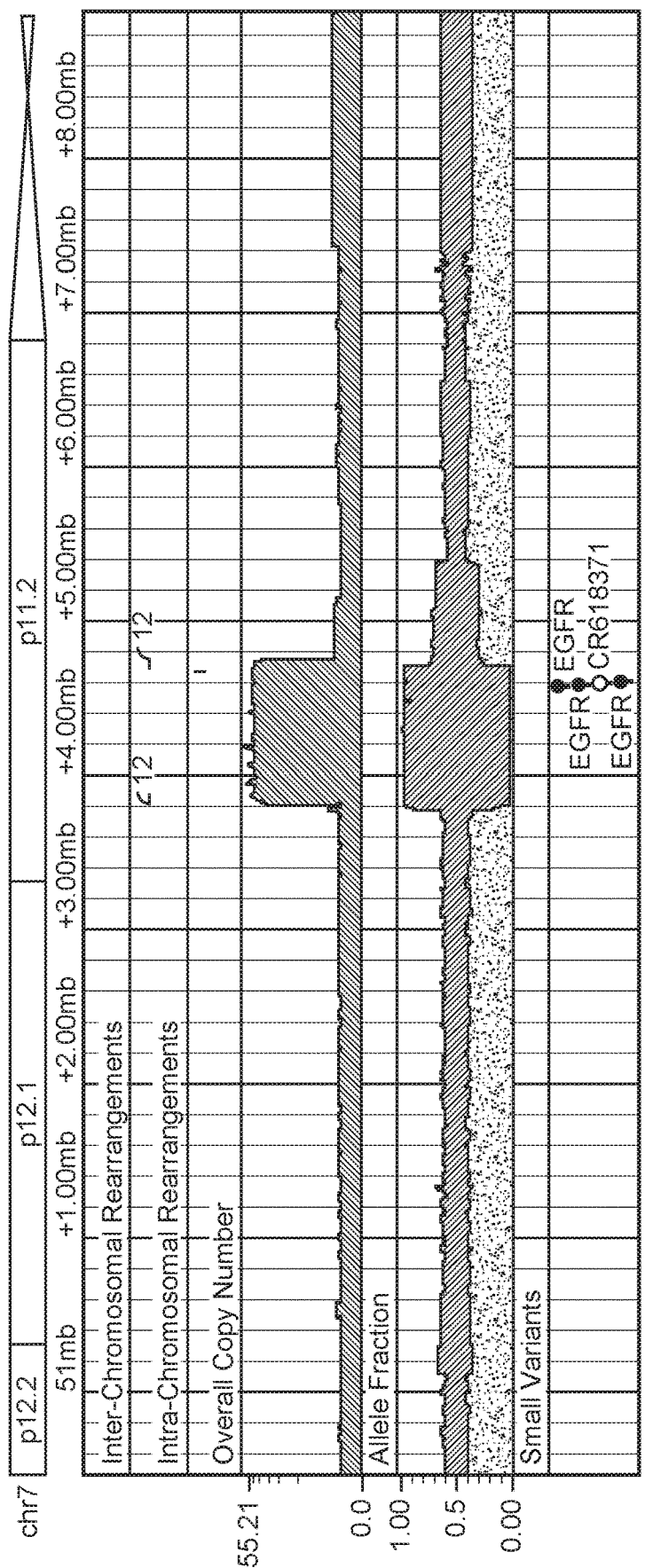
Figures 1, 10B:
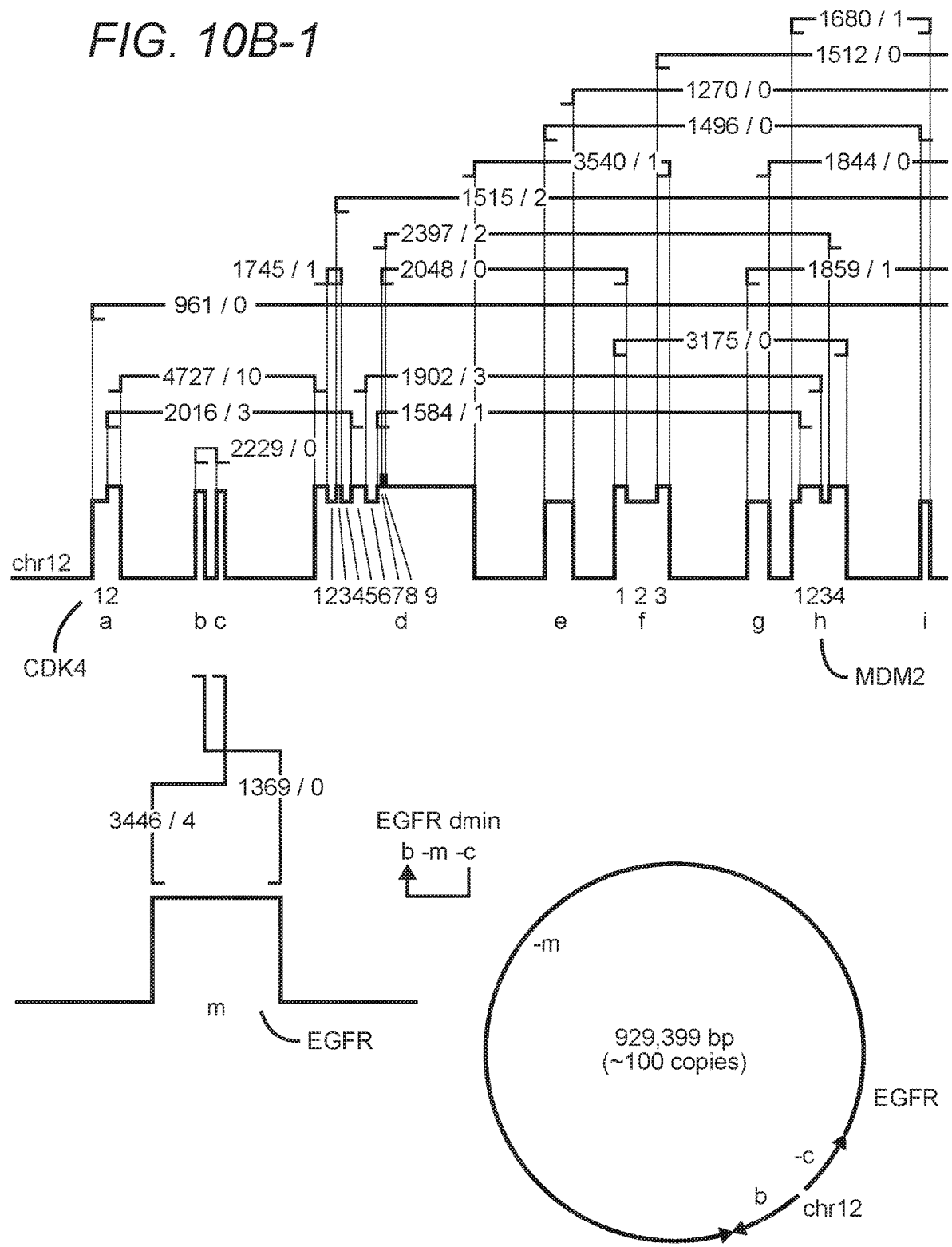
Figures 2, 10B:
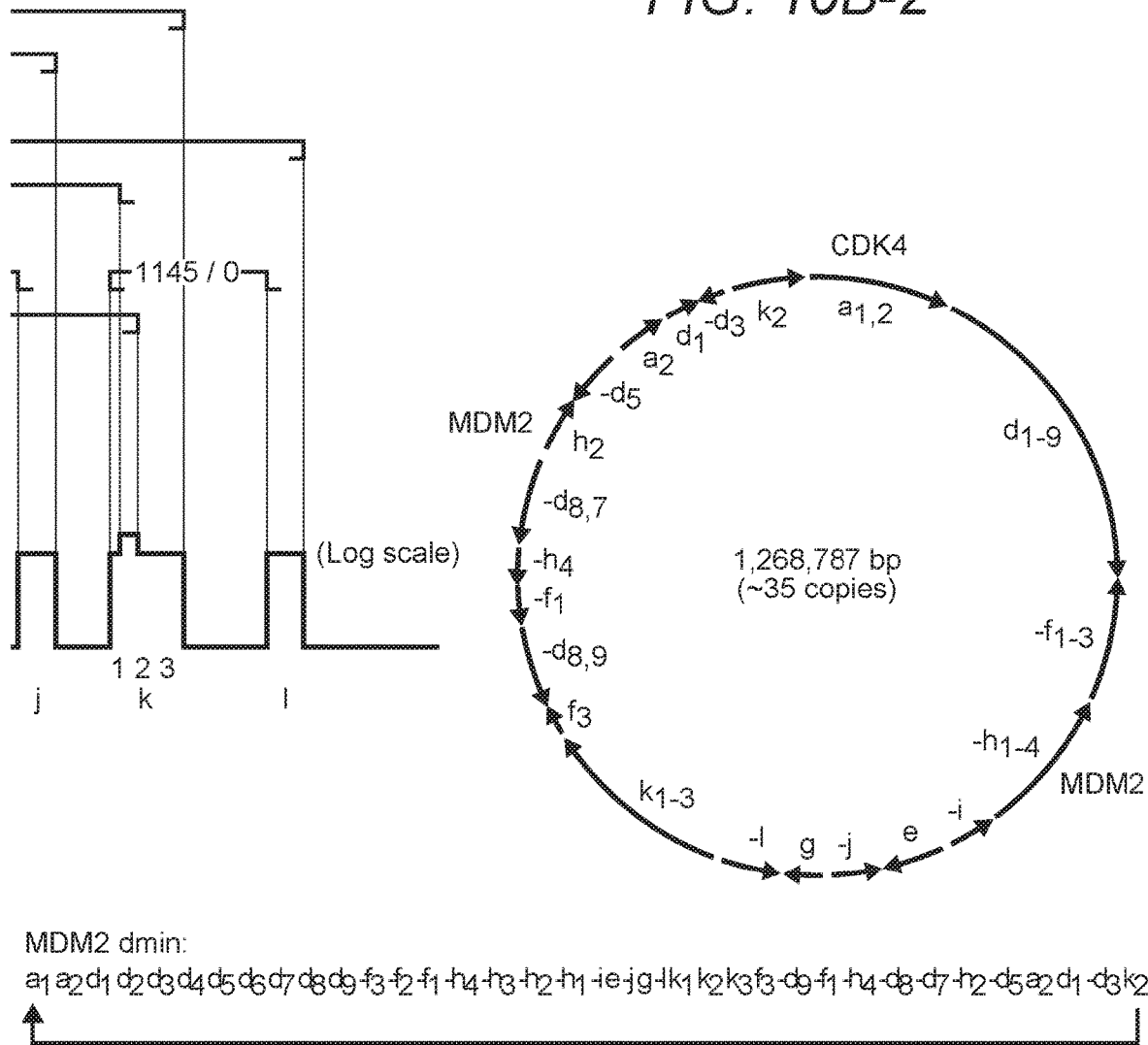
Figures 1, 11A:
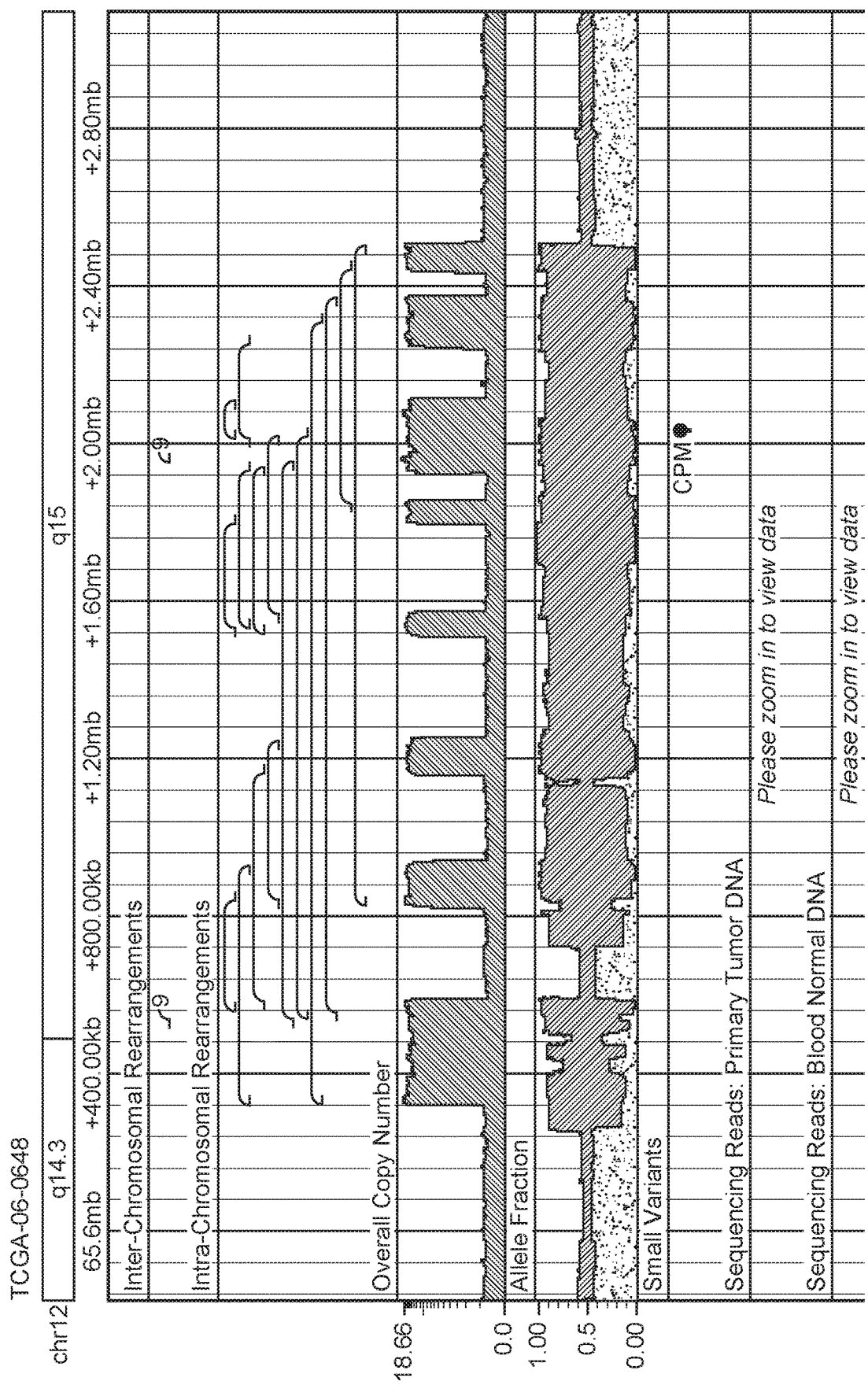
Figures 2, 11A:
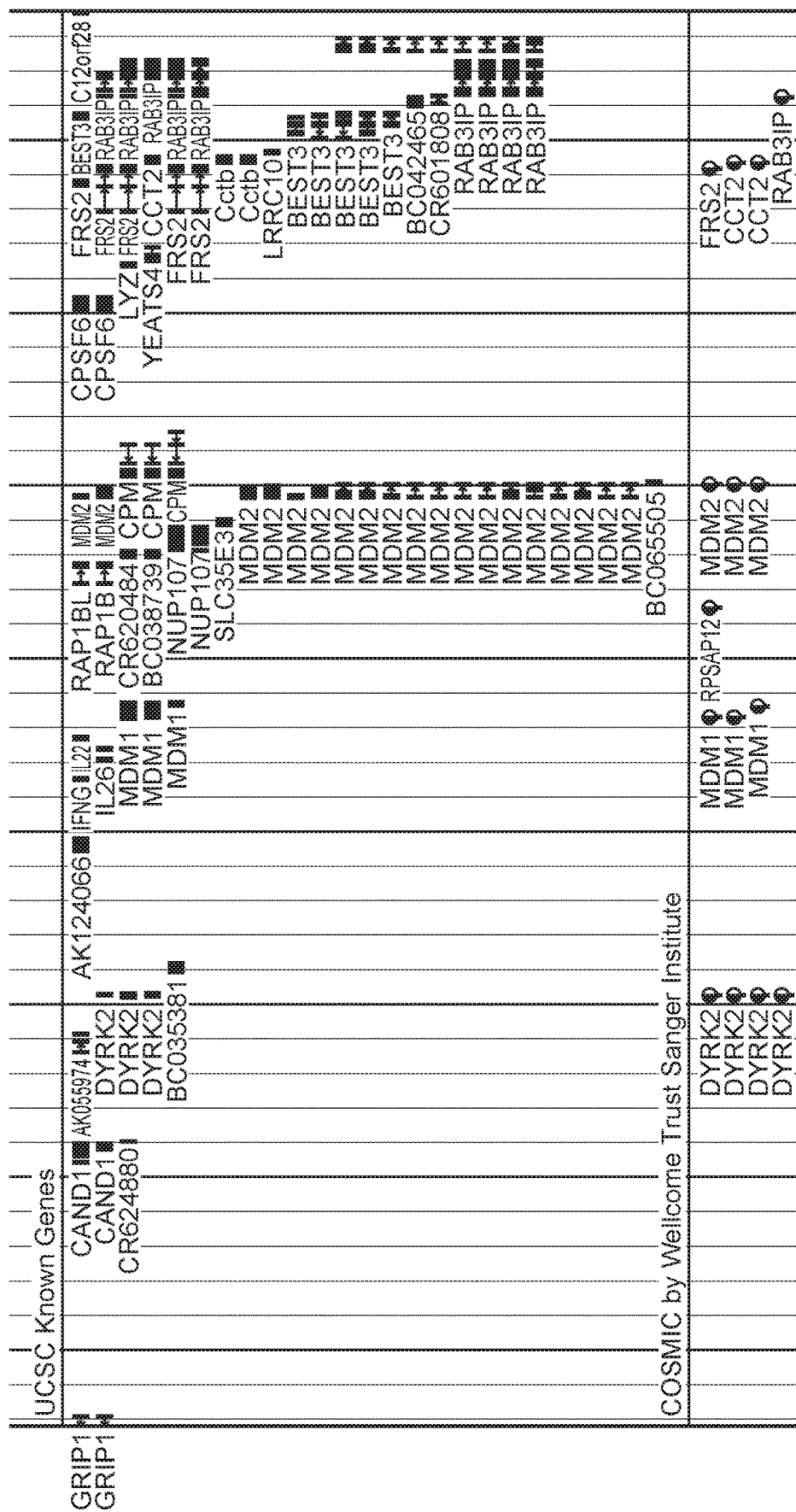
Figures 2, 11B:
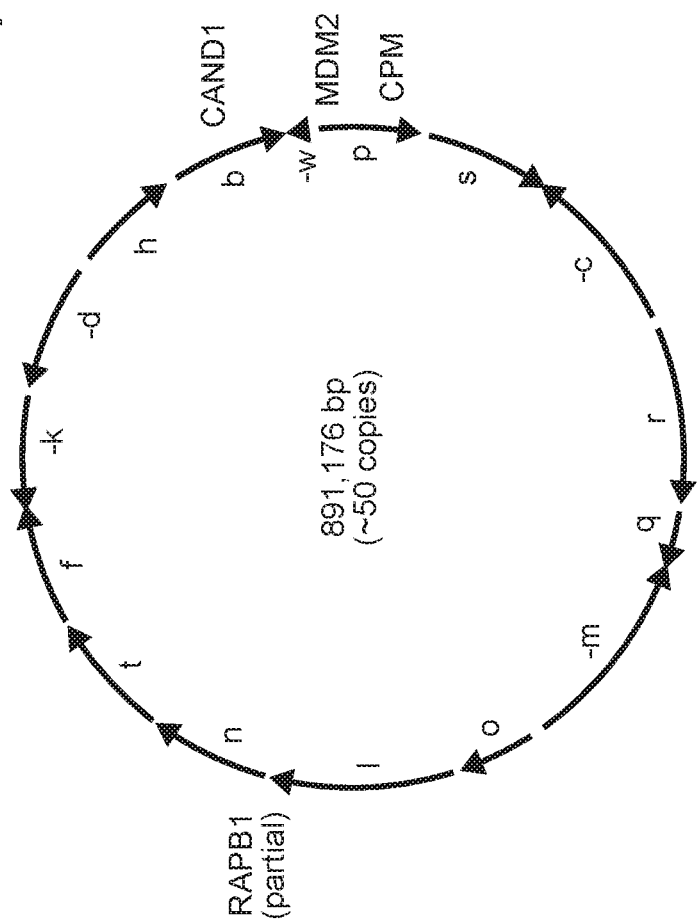

For each unaligned read, the dual spanning sets determine a potential location of the breakpoint. Since each unaligned read may determine slightly different locations for the breakpoint (due to sequence errors near the breakpoint, repetitive reference, etc.), all breakpoint locations determined from the dual-spanning sets are used to generate possible junction sequences. All unmapped reads are newly aligned to each of these possible junction sequences and the overall improvement in their alignments is measured against how well the reads aligned to the original sequences. The junction sequence that yields the greatest improvement in alignment scores is judged as the best candidate for the true rearrangement. If this best junction sequence yields negligible improvement in the alignment scores, then this junction sequence is discarded as it is unlikely to represent the true rearrangement. In this case, it may also be determined that the lack of split read confirmation is evidence that the original structural rearrangement found by bambam could be spurious. FIG. 2 schematically depicts an exemplary method to precisely identify the locations in the genome where the structural rearrangement occurred. Tiles (or kmers) are determined for both the potential split read and the reference genome. Dual-spanning sets are determined (represent as the thick red and purple boxes on the bottom of this figure), which fully define how to construct the rearranged sequence. Dual-spanning sets are robust to sequence errors or SNPs in the split read.

Once structural variations have been refined using split-reads as described above, one or more breakpoints are determined that are indeed related to highly amplified regions. More specifically, the support of a given breakpoint is directly proportional to the copy number of the regions it connects. Thus, by requiring breakpoints to have a high level of read support, one can can filter out breakpoints that are part of a copy-neutral rearrangement or led to low-copy amplifications and deletions to instead focus on the breakpoints that are part of highly amplified regions in the tumor. The particular read support threshold is chosen such that breakpoints that have read support expected of copy-neutral regions of the tumor genome are removed.

Amplicons can then be reconstructed by walking the breakpoint graph. For example, and similar to a recently published method (Genome Res. 2011 Oct. 12), the inventors constructed a breakpoint graph by describing a set of edges that represent the amplified segments of the tumor genome and a set of directional vertices that connect the edges to one another. Here, the edges are defined as the amplified segments of the tumor genome observed in the relative copy number, while the vertices are the highly supported breakpoints found in the manner described above. If an amplified segment is interrupted by a breakpoint, then that segment will be split into two edges at the location of the interrupting breakpoint.

With the segments laid out according to genomic position, the inventors determined the arrangement of edges that represent the rearranged tumor sequence by starting at the leftmost position of the first amplified segment and progress towards the right until a right-oriented vertex is encountered. The path continues by following the vertex to the segment it is connected to and moving in the direction (left or right) specified by the outgoing vertex. A solution to the breakpoint graph is made when a path through all edges and vertices have been traversed at least once. A toy example breakpoint graph and its solution are shown in FIG. 3, demonstrating walking the breakpoint graph to reconstruct a rearranged sequence. Starting with segment "a", one will follow the exiting breakpoint 1 to the right, which enters the left-hand side of segment "b." Continuing to the right, one will follow the exiting breakpoint 2 that enters the right-hand side of segment "c." This breakpoint points to the left, indicating that segment "c" is found in an inverted orientation in the rearranged sequence. The final breakpoint 3 is followed back to the left-hand side of segment "a," accounting for all extra copies in the copy number. The final solution found is thus "a b-c".

Given such loose constraints, it is clear that many satisfactory solutions to the breakpoint graph may be possible. However, the optimal path(s) through the graph are those that most closely agree with the observed relative copy number. The number of times a solution traverses a given segment produces an estimate of that segment's copy number. The root mean square deviation (RMSD) of the segment traversal counts to the observed relative copy number for each solution is calculated, and then the solution(s) with the smallest RMSD value are labeled as optimal.

Examples

The inventors applied the above described methods to two glioblastoma multiforme (GBM) samples designated TCGA-06-0648 and TCGA-06-0152, both sequenced by The Cancer Genome Atlas (TCGA) project. The tumor and matched normal (blood) sequencing datasets from these samples were processed as described in Methods, producing tumor vs. normal relative copy number estimates, identifying breakpoints, and performing split read analysis. The tumor and normal genomes of both samples were sequenced to an average coverage of approximately 30×.

A total of 3,696 breakpoints were identified by bambam, of which 132 breakpoints were found by bridget to have split reads directly spanning the putative breakpoint. FIG. 4 shows a histogram of read support for all somatic breakpoints found in sample TCGA-06-0648. By setting the minimum read support threshold to 100, all but 16 of the somatic breakpoints supported by bridget were removed. Interestingly, all 16 of these highly supported breakpoints are near the boundaries of highly amplified segments in a clustered region of chromosome 12, as shown in FIG. 5, where the genome browser displays relative copy number ("Overall Copy Number", in gray) and highly supported breakpoints ("Inter-Chromosomal Rearrangements" and "Intra-Chromosomal Rearrangements," with breakpoint support>100 reads) for sample TCGA-06-0648. A total of 16 amplified segments are found, with one segment containing the known oncogene MDM2 implicated in GBM tumorigenesis. In fact, the boundary of every amplified segment can be associated with a single breakpoint that is correctly oriented such that it enters into or exits from the amplification. This suggests that the highly supported breakpoints and the amplifications are related and may in fact represent the rearranged configuration of the amplified segments in the tumor's genome.

Figure 6:
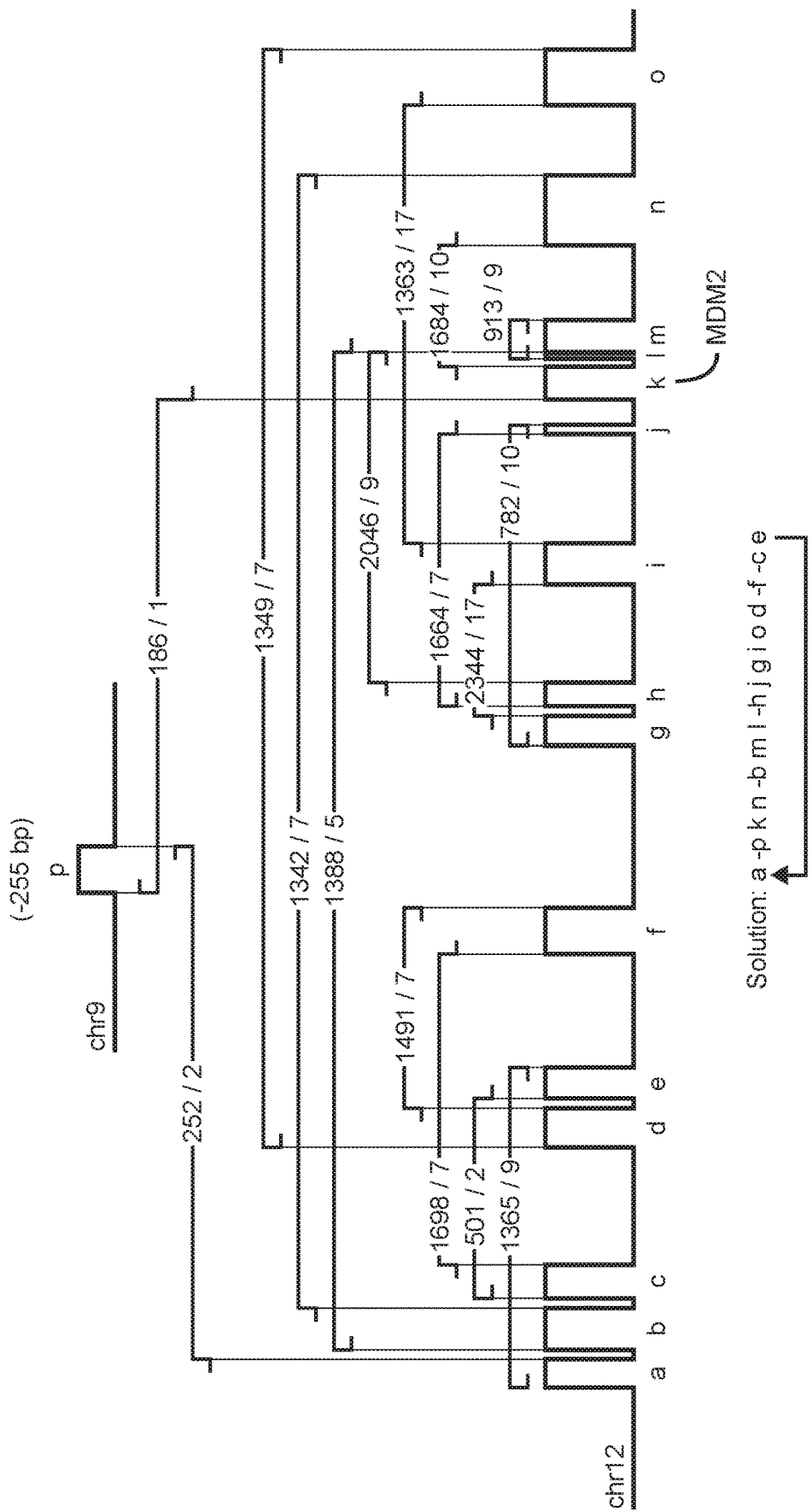
FIG. 6 is a detail view of the data shown in FIG. 5 and a circular solution for the breakpoint graph.

FIG. 6 is a diagram of these same data that exaggerates the size and location of some segments as they are too close together to be visualized in the browser plot of FIG. 5. FIG. 6 depicts a circular solution of TCGA-06-0648 breakpoint graph suggesting the presence of an amplified double minute chromosome containing MDM2. Breakpoint read support is listed as Tumor read count/Blood read count, e.g., 1365/9 means that 1,365 reads support the breakpoint in the tumor and 9 supporting reads are found in the blood. The solution lists the order and orientation of the segments in their new configuration, with the minus symbol used to indicate a segment in an inverted orientation. The copy number of the amplified segments suggests there are at least 40 copies of each segment present in the average tumor cell. This diagram is a visual representation of the breakpoint graph, and by walking the breakpoint graph, a single optimal solution is found. The interesting aspect of this solution is that it is circular, in that the final traversal of last segment returns back to the starting position, i.e. the first vertex is also the final vertex. The circular solution passes through every segment exactly once, yet the copy number suggest there are approximately 40 copies of each segment in the tumor genome. To account for those extra copies, one must loop through the segments for another 39 passes. These additional copies could be present in many different configurations, exemplified by two extremes: (1) 40 copies were replicated to form an unbroken tandem array of these segments in this precise order and orientation, or (2) a single, self-replicating double minute chromosome was formed of which the average tumor cell has accumulated 40 copies. Clearly the latter option is more parsimonious, as it doesn't require 40 successive tandem duplications to occur at approximately the same location in the rearranged sequence (i.e. the bounding vertices of the initial amplicon) such that no amplified segments are lost or exist at different concentrations. Therefore, the data suggest an oncogenic DM containing MDM2 exists in this GBM tumor sample.

Also shown on FIG. 6 are the read supports for all highly supported breakpoints in both tumor and blood sequencing datasets. First note that the breakpoints have incredibly high support in the tumor, with some breakpoints supported by more than 2,000 split reads. This is to be expected since the rearrangements define the amplicon, and the amplicon is present at very high copy number. More interesting is that every breakpoint also shows a surprisingly high amount of support in the patient's blood. Given the propensity of DMs to getting lost after successive stages of mitosis, it is unlikely that the DM was present originally in the germline and maintained for decades, only to undergo amplification during tumorigenesis. This is especially true considering that oncogenic DMs are unlikely to provide a selective advantage to non cancerous cells. A more parsimonious solution is that this oncogenic DM is instead somatic in origin, constructed and amplified at some point prior or during tumorigenesis. The selective advantage this DM provided to the emerging tumor cell led to cells that accumulate more copies of the DM having a distinct growth advantage over those that had fewer, resulting in a population of tumor cells with the uniformly high copy number observed in the regions assumed to be part of this DM. The fact that MDM2 is often found in oncogenic DMs lends further support for this hypothesis (Genomics. 1993 Febuary; 15(2):283-90).

Figure 7:
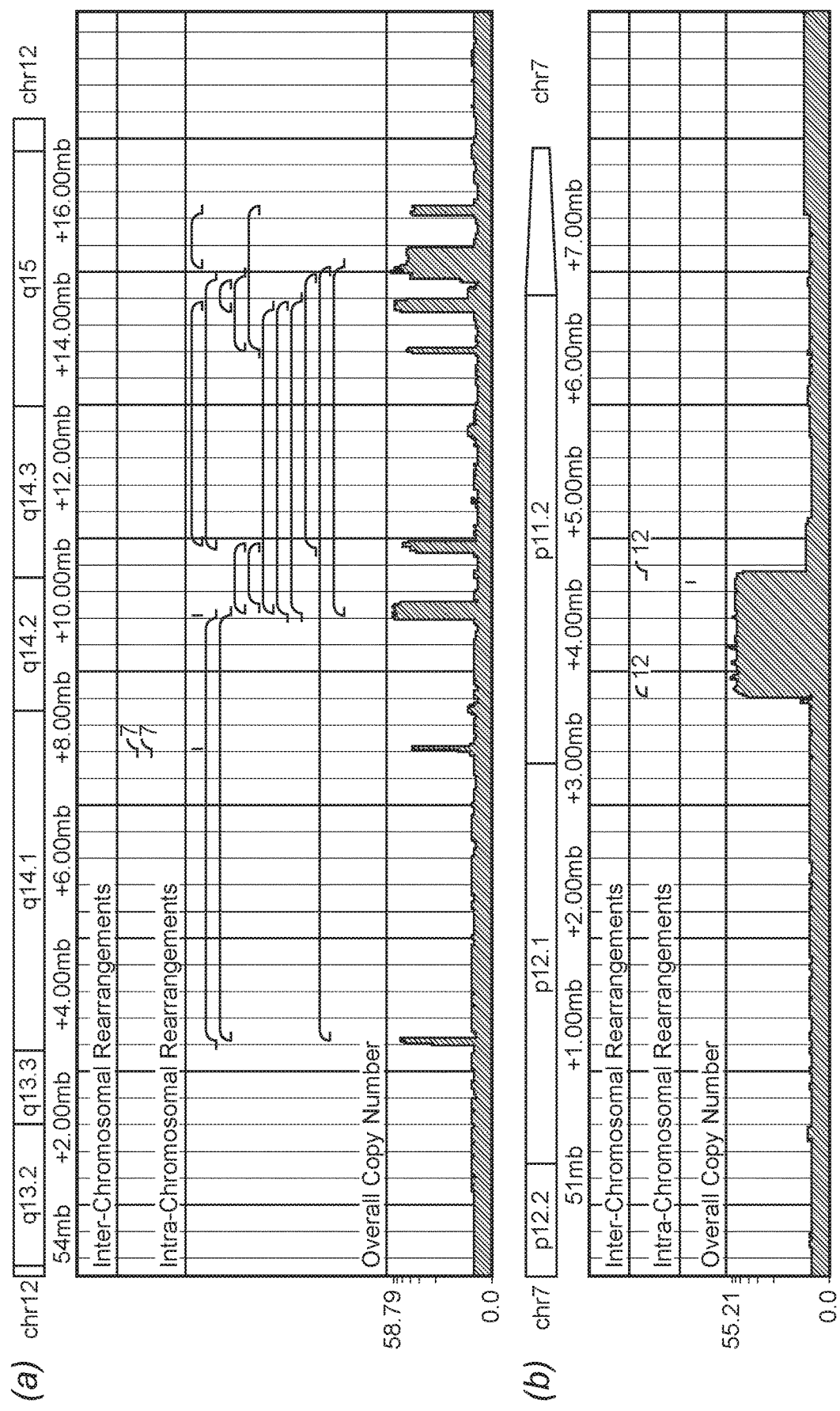
FIG. 7 depicts exemplary genome browser displays depicting high copy numbers and highly supported breakpoints on chromosomes 7 and 12.
Figure 8:
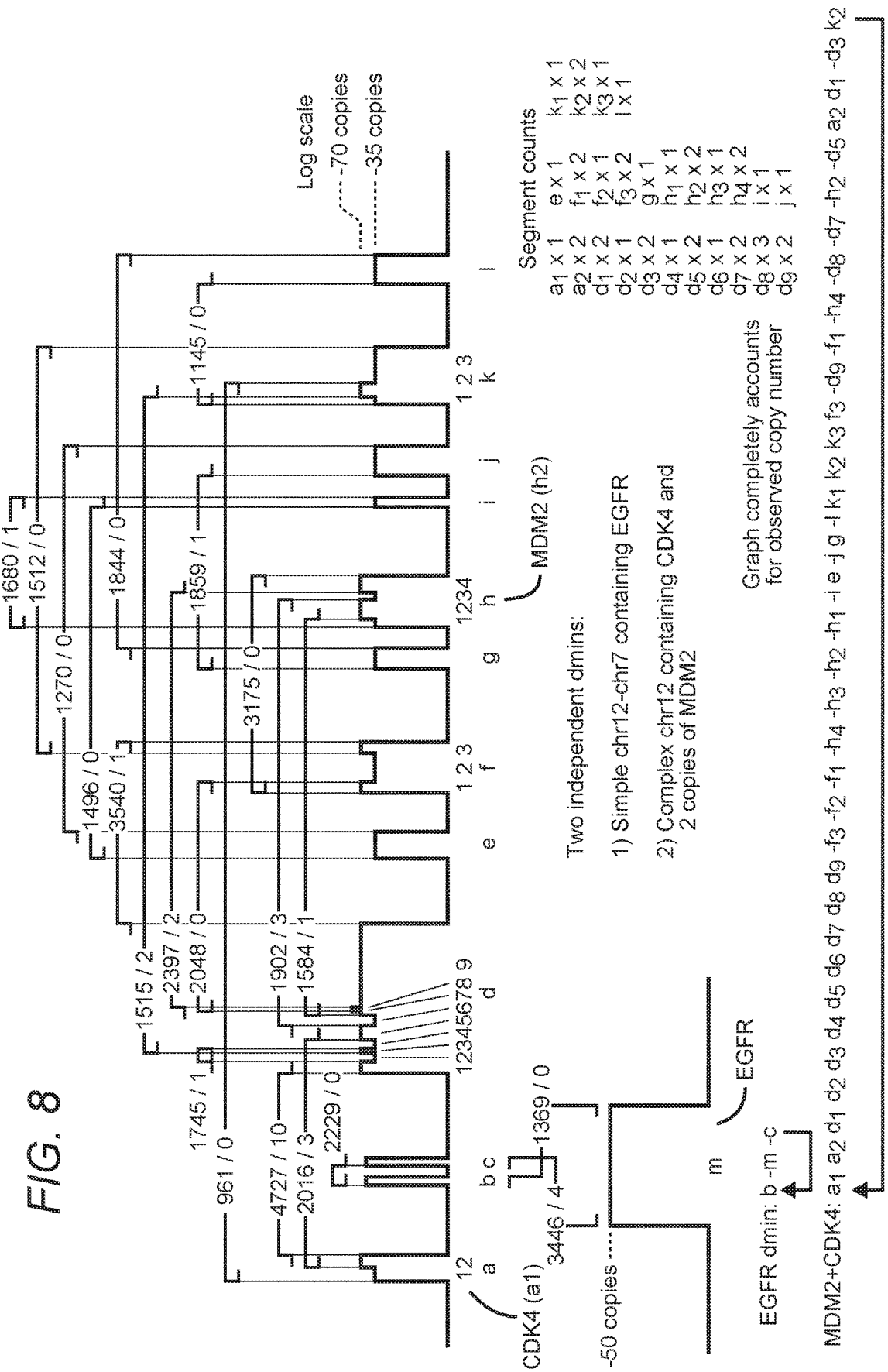
FIG. 8 is a detail view of selected data shown in FIG. 7 and circular solutions for the breakpoint graph.

Similar results in the other GBM tumor sample, TCGA-06-0152, processed by the methods described here. Shown in FIG. 7 are browser shots of highly amplified regions on chromosome 12 that include oncogenes CDK4 and MDM2 and a region of chromosome 7 that includes the EGFR oncogene. Here, the genome browser plot of the amplified segments and highly supported structural variants (read support>100) for sample TCGA-06-0152 on chromosomes (a) 12 and (b) 7 is shown. Note the inter-chromosomal breakpoints in purple that connect a small amplified region on chr12 with the amplified region on chromosome 7, which contains EGFRA diagram of these regions is given in FIG. 8. Here, circular solutions of the breakpoint graph for GBM sample TCGA-06-0152 are shown that suggest the presence of two separate oncogenic DMs amplified in the tumor. The solution of the MDM2+CDK4 double minute traverses some segments multiple times, but all extra traversals are accounted for the in the observed relative copy number. 11 of the 20 breakpoints show discordant read evidence in the patient's blood sample. In total, 29 segments on the two chromosomes were amplified, with some segments display much higher relative copy numbers than others. 20 highly supported breaks are found and, as before with sample TCGA-06-0648, all breaks can be uniquely associated with a discontinuity in the relative copy number. By solving the breakpoint graph, two independent circular solutions were found. Solution (1) uses all but two intra-chromosomal breakpoints on chromosome 12 and contains one copy of the oncogene CDK4 and two copies of the oncogene MDM2. Solution (2) incorporates the two inter-chromosomal breakpoints spanning amplified regions on chromosome 7 and 12 and two intra-chromosome breakpoints on chromosome 12, and contains the oncogene EGFR. These two solutions suggest that two DMs were formed and amplified in this sample, both of which contain different oncogenes and likely provided significant selective advantage to the growing tumor cells.

Solution (1) also describes a much more complicated path through the amplified segments than observed in sample TCGA-06-0648. To incorporate all highly supported breakpoints in the solution, some segments had to be traversed multiple times. 11 of the 29 segments were traversed two times, and one small segment was traversed three times. The increased copy number that would be expected by these traversals is observed in the relative copy number, where the average tumor cells containing approximately 35 copies of this DM. The segments that are traversed twice have a copy number of roughly 70. The segment traversed three times appears to have increased copy number compared to the twice-traversed segments (~85 vs. ~75), but the small size of this segment makes it difficult to compute accurate relative copy number.

As before, there is evidence of tumor breakpoints in the blood sample of patient TCGA-06-0152, but to a lesser degree than observed in the blood sample of TCGA-06-0648. 11 of the 20 breakpoints have low levels of read support, while 9 breakpoints have no read support in the blood. There are numerous reasons why this could be the case. For instance, the blood data may have been sequenced at lower coverage, resulting in a lower chance of sequencing across any given somatic breakpoint. Alternatively, the reason may be biological in nature, whereby some mechanism induced the TCGA-06-0152 tumor to shed DMs into the bloodstream at a lower rate than TCGA-06-0648, reducing the observed concentration of DMs in the blood.

The presence of tumor discordant reads in the blood of DM-specific breakpoints then suggests that these GBM-borne DMs are crossing the blood-brain barrier and entering the patient's bloodstream. Most tantalizing is that the number of GBM-borne DMs in the blood is such that DM-specific breakpoints are detectable using sequencing data at average coverage derived only from the blood of the patient. Although the sequencing evidence strongly suggests the presence of oncogenic DMs, FISH (fluorescence in situ hybridization) analysis of the amplified oncogenes would have to be performed on both tumor and matched normal samples to confirm this hypothesis.

Viewed from another perspective, it should be appreciated that genome instability and structural rearrangement is a distinctive hallmark of the cancer genome. With next-generation sequencing technologies, the inventors' ability to measure structural rearrangements that occur through tumorigenesis and progression has significantly improved, however created an urgent need for rearrangement discovery, analysis, and visualization methods to aid better comprehension of these events.

To address these challenges, the inventors' sequencing analysis pipeline streamlines the discovery of individual tumor's mutations, small indels, copy number alterations, allele-specific amplifications and deletions, and genomic rearrangements. For example, in one representative analysis, rearrangements are refined to breakpoint precision using unmapped, putative split reads found in the vicinity of the breakpoint when available. The results are then presented, preferably in an interactive, web-based genome browser that provides analysis and visualization of both high-level, processed results as well as the raw data from which they were derived, which is schematically illustrated in FIG. 9.

The sequencing analysis pipeline was used to discover high-confident, small- and large-scale somatic events in 17 whole genome glioblastoma multiforme (GBM) tumor samples from The Cancer Genome Atlas (TCGA) project, using their matched normal sequences to identify somatic rearrangements. Among many interesting structural aberrations identified in these samples, the inventors found two tumors with complicated rearrangement patterns in regions of extreme amplification that could be assembled to construct circular double minute chromosomes at base-level precision as can be seen in FIGS. 10A/B and 11A/B. Evidence of breakpoints specific to the double minute were found in blood sequencing data, raising the possibility that patient-specific PCR-based assays could be developed to quantify the presence of somatic rearrangements to use as a proxy in monitoring the progression of brain tumors.

Figures 1, 12A:
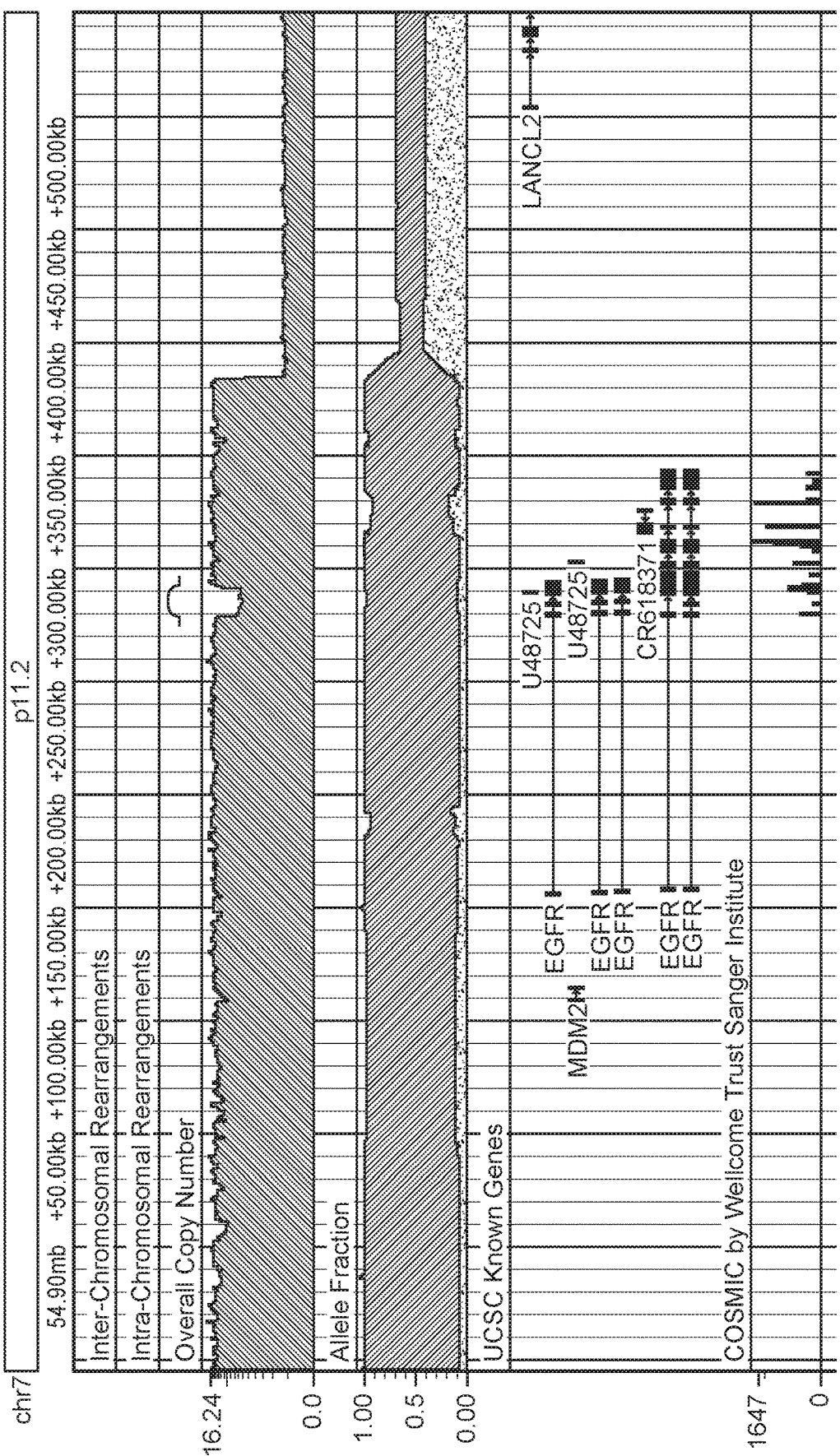
Figures 2, 12A, 12B:
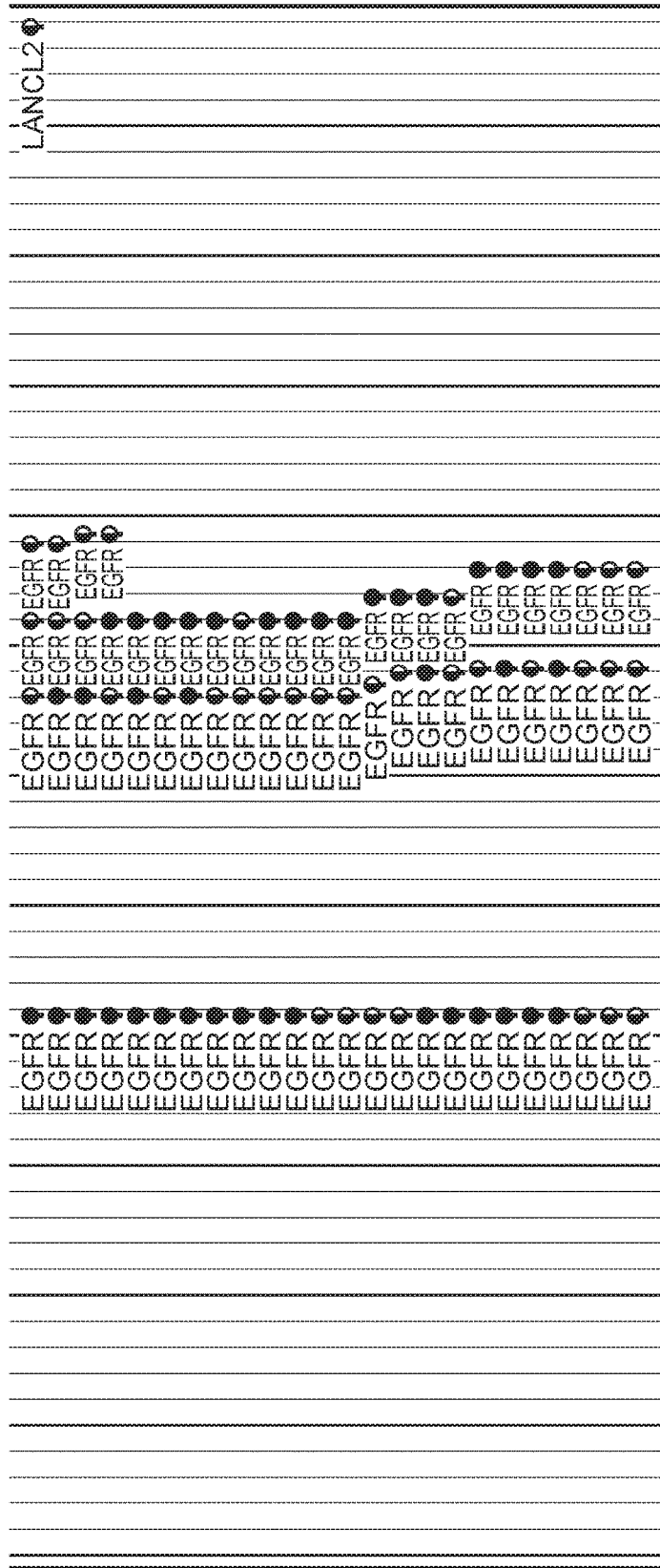

Also, four GBM tumors were found exhibiting EGFR amplifications and rearrangements indicating the presence of the EGFRvIII mutant gene, whereby exons 2-6 of EGFR are deleted. Comparing the read support of the EGFRvIII associated breakpoints to the amount of normally mapped reads in the neighborhood suggest that the EGFRvIII mutant emerges after the amplification of wild-type EGFR, existing as a fraction of the total number of EGFR copies in the tumor. Exemplary results are presented in FIG. 12A/B.

Therefore, it should be appreciated that the ability to integrate relative copy number with breakpoints provides a new way to understand the genomic topology of the cancer cell. More specifically, the inventors demonstrated that, in the case of highly amplified regions of the tumor, both the observed copy number and highly supported breakpoints can be completely explained by solving a simple breakpoint graph, which describes the order and orientation of the highly amplified segments in the tumor genome.

In the GBM samples discussed here, the optimal solutions to the breakpoint graphs of amplified segments are circular. These circular solutions suggest that the observed amplified regions may have formed a circular chromosome called a double minute. The presence of oncogenes on each double minute and their highly amplified state indicate that the double minutes have strong oncogenic potential, confer a selective advantage to the tumor cell, and their formation were likely a key event in the tumorigenesis of both GBM tumors.

Equally important to the reconstruction of a part of these tumor genomes that likely had an enormous impact in the development of both tumors, is the fact that nearly every breakpoint specific to the DMs also has detectable read support in the blood of that patient. This finding suggests that GBM-borne DMs are entering the bloodstream by some mechanism, which is especially significant since it suggests that GBM tumors featuring oncogenic DMs may be detected and monitored using blood samples without requiring prior tumor sequencing.

One possible transport mechanism for these oncogenic DMs is via microvesicles, which are extracellular fragments of the plasma membrane shed from most cell types that can contain various cellular components. Studies have shown that tumor cells release an abundance of microvesicles containing multiple sub-cellular particles, including nucleic acids and proteins, that have the potential to be used for diagnostics and monitoring. Initially mRNA, miRNA and angiogenic proteins were identified in serum taken from patients with GBM tumors (Nat. Cell Biol. 2008 December; 10(12):1470-1476). More recently, Balaj et al (Nat Commun 2011; 2:180) have isolated microvesicles containing single-stranded DNA (ssDNA) with amplified oncogenic sequences, in particular c-Myc.

The ability to detect DMs in the bloodstream should extend to other cancers that commonly feature highly amplified DMs containing known oncogenes, such as EGFR in non-small cell lung cancer and c-Myc in acute myelogenous leukemia. In fact, the ability to detect DMs with this method may improve for tumor types where the bloodstream is more accessible. Furthermore, drugs that specifically target genes commonly amplified via DM-based mechanism may be prescribed based on evidence collected solely from the bloodstream, avoiding painful, and in the case of GBM tumors, dangerous tumor biopsies.

One can envision sequencing-based assays that incorporate whole-genome sequencing data of blood samples to reliably determine if a region surrounding known oncogenes, such as EGFR, c-Myc, MDM2, etc., exhibit a clustered pattern of breakpoints indicative of an amplified double minute. Combining discordant reads across such regions should improve the ability to identify these regions even when the concentration of DMs in the bloodstream is low. If microvesicles indeed transport DMs, then techniques to enrich for microvesicles will further improve the ability to detect low levels of oncogenic DMs from blood samples.

Therefore, based on the above, it should be appreciated that the molecular diagnostic tools presented herein can be employed in the diagnosis and/or confirmation of a neoplastic disease without prior knowledge of the disease. Most preferably, the biological sample is blood or serum/plasma fraction of blood, but may also include biopsy material or aspirates. Still further, it is contemplated that such diagnostic methods may be suitable for all types of neoplastic diseases, and especially cancers (e.g., various carcinomas, lymphomas, and sarcomas).

Consequently, the inventors especially contemplate the use and/or identification of one or more rearrangement patterns of genetic information, where most preferably, the genetic information is directly obtained from whole blood (or a processed fraction thereof). Most typically, the rearrangement patterns include genomic rearrangement, particularly where a circular molecule is formed from genomic material (typically having a size of equal or less than 3 Mb). In especially contemplated uses and methods, the circular rearranged genetic material includes at least a portion of an oncogene and/or tumor suppressor gene. However, and most typically, the circular rearranged genetic material will include a fully functional or at least fully expressable form of an oncogene and/or tumor suppressor gene. Thus, a sample of a mammal can be analyzed in various therapeutic, diagnostics, or prognostic methods (preferably using a simple blood test that detects double minutes, and particularly double minutes that include an oncogene and/or tumor suppressor gene. Conversely, and premised on the observation that tumor bearing individuals have double minutes in the blood stream (and particularly double minutes that include an oncogene and/or tumor suppressor gene), it should be recognized that new or heretofore unidentified oncogenes and/or tumor suppressor genes may be discovered from analysis of double minutes isolated from tumor bearing individuals (or even cell cultures or animal models).

Based on further observations, the inventors also contemplate that a numerical ratio of double minutes relative to genomic information may be employed as a threshold for indication of a disease, and particularly a neoplastic disease. Thus, analysis of double minutes may be used as a leading indicator to predict risk or spread of cancer. Of course, it should be noted that the double minute need not necessarily include an oncogene and/or tumor suppressor gene for such analysis.

Moreover, it is contemplated that the type of oncogene in a double minute might also be associated with a particular type of disease, and especially neoplastic disease. Thus, analysis of genetic rearrangements from whole blood and identification/quantification of an oncogene and/or tumor suppressor gene in the double minute may provide valuable information on the type, progression, and/or risk of a particular neoplasm. Therefore, numerous whole blood-based tests (e.g., no separation, filtering, etc.) are deemed particularly useful for detection of an oncogene in the diagnosis or prediction or a disease. For example, upon establishment of specific breakpoints and rearrangements that are characteristic to a particular tumor type, primers could be designed that specifically help indentify presence and/or quantity of such rearrangements (and DM). Similarly, therapeutic efficiency or drug effects may be determined in methods using analysis of double minutes, and especially those that include an oncogene and/or tumor suppressor gene. Such methods of testing may be particularly useful in the context of certain chemotherapeutic and/or radiation treatment, which is predicated on double strand breaks (or inhibition of repair thereof).

Based on the observation that double minutes can be isolated from whole blood in substantial quantities, the inventors also contemplate that the double minutes may be associated with proteins, lipoproteins, lipids, and/or vesicle structures, and particularly microvesicles. Thus, and where the double minutes are encapsulated in microvesicles, it should be appreciated that the surface epitopes from the microvesicles are representative of the cells from which the microvesicles originated. Consequently, the tumor origin (e.g., tissue type) can be identified based on analysis of microvesicle membrane components.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of analyzing genomic data of a double minute chromosome that originates from a solid tumor to thereby treat an individual having the solid tumor, the method comprising:
    obtaining from the individual a biological fluid comprising a double minute chromosome, wherein the double minute chromosome originates from the solid tumor;
    associating a copy number of a tumor genomic sequence present in the biological fluid with a breakpoint in the tumor genomic sequence upon reaching a read support threshold for the breakpoint, and determining an orientation of the tumor genomic sequence;
    using the breakpoint, the copy number, and the orientation to reconstruct the double minute chromosome;
    determining a breakpoint junction that connects a first end of a first segment in the tumor genomic sequence with a second end of a second segment in the tumor genomic sequence; and
    administering to the individual a drug that targets a gene in the double minute chromosome, to treat the solid tumor.

2. The method of claim 1 further comprising a step of using the breakpoint junction to identify the drug.

3. The method of claim 2 wherein the step of identifying the drug comprises identifying an oncogene or tumor suppressor gene in the rearrangement pattern.

4. The method of claim 2 wherein the step of identifying the therapeutic treatment option comprises identifying a peptide sequence in the rearrangement pattern.

5. The method of claim 1 wherein the biological fluid is blood.

6. The method of claim 1 wherein the read support threshold for the breakpoint is at least 100 reads.

7. The method of claim 1 wherein said reconstructing the double minute chromosome is performed using a breakpoint graph.

8. The method of claim 1 wherein the double minute chromosome is in a circulating tumor cell or in a microvesicle.

9. The method of claim 1 wherein the double minute chromosome comprises an oncogene or a tumor suppressor gene.

* * * * *